(12) United States Patent
Ulevitch et al.

(10) Patent No.: US 6,168,790 B1
(45) Date of Patent: *Jan. 2, 2001

(54) USE OF ANTIBODIES TO BLOCK THE EFFECTS OF GRAM-POSITIVE BACTERIA AND MYCOBACTERIA

(75) Inventors: Richard J. Ulevitch, Del Mar; Peter S. Tobias, San Diego, both of CA (US); Jerome Pugin, Puplinge (CH)

(73) Assignee: The Scripps Research Institute, La Jolla, CA (US)

( * ) Notice: Under 35 U.S.C. 154(b), the term of this patent shall be extended for 0 days.

This patent is subject to a terminal disclaimer.

(21) Appl. No.: 09/099,957

(22) Filed: Jun. 19, 1998

Related U.S. Application Data

(63) Continuation of application No. 08/307,931, filed on Sep. 16, 1994, now abandoned, which is a continuation-in-part of application No. 07/990,378, filed on Dec. 15, 1992, now abandoned.

(51) Int. Cl.[7] .................................................. A61K 39/40
(52) U.S. Cl. ................... 424/150.1; 424/9.2; 530/388.4; 530/388.25
(58) Field of Search ................................ 424/150.1, 9.2; 435/70.21; 530/388.4, 388.25

(56) References Cited

U.S. PATENT DOCUMENTS

| | | | |
|---|---|---|---|
| 5,436,321 | * 7/1995 | Wright | 530/388.25 |
| 5,730,980 | * 3/1998 | Ulevitch et al. | 424/154.1 |
| 5,820,858 | * 10/1998 | Leturcq et al. | 424/133.1 |

FOREIGN PATENT DOCUMENTS

9101639 * 2/1991 (WO).

OTHER PUBLICATIONS

Heumann et al. Infection and Immunity 62(7):2715–21, 1994.*

Natanson et al. Journal of Clinical Investigation 83:243–51, 1989.*

Zhang et al. Journal of Clinical Investigation 91:2076–83, 1993.*

* cited by examiner

Primary Examiner—Lynette R. F. Smith
Assistant Examiner—Ginny Allen Portner
(74) Attorney, Agent, or Firm—Gray Cary Ware & Freidenrich LLP; Lisa A. Haile

(57) ABSTRACT

The present invention concerns a method of treating bacteremia, sepsis and other forms of toxemia caused by Gram-positive bacteria and mycobacteria comprising administering a therapeutically effective amount of anti-CD14 antibody molecules. A therapeutic composition comprising anti-CD14 antibody molecules in a pharmaceutically acceptable excipient is also contemplated.

3 Claims, 19 Drawing Sheets

FIG. 3

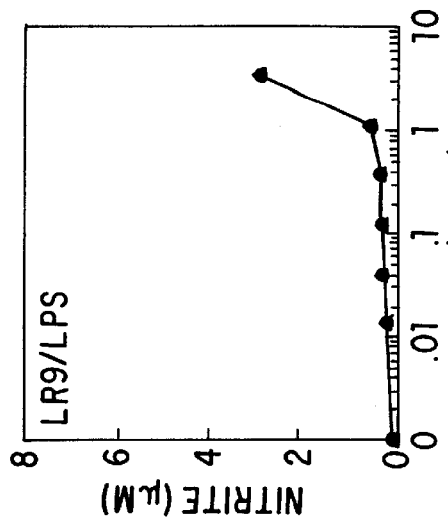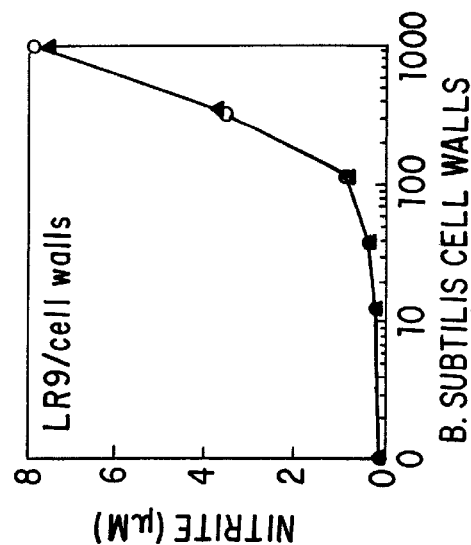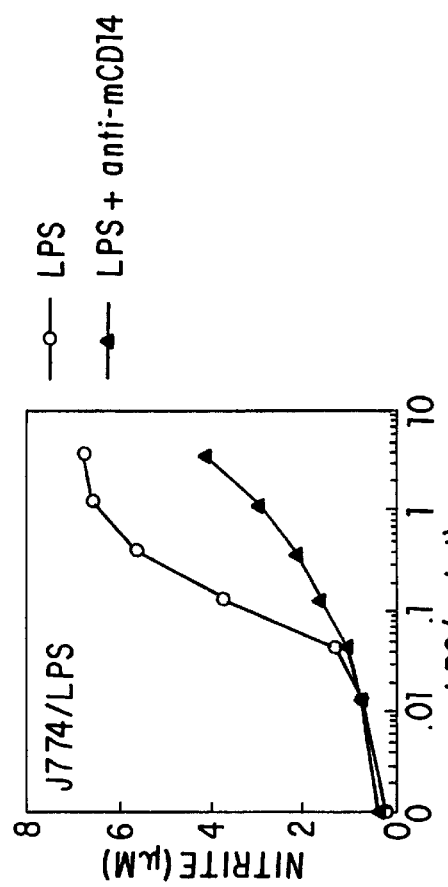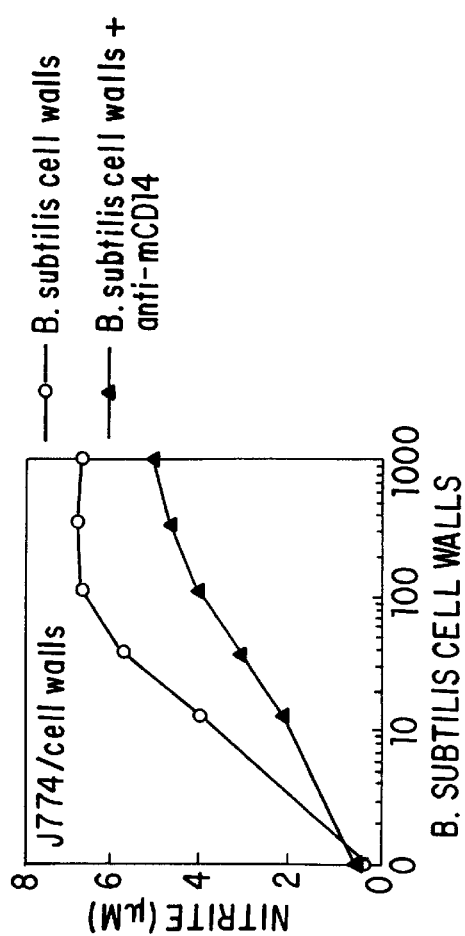
FIG. 11A
FIG. 11B
FIG. 11C
FIG. 11D

SEQUENCE LISTING

```
<160> NUMBER OF SEQ ID NOS:  3

<210> SEQ ID NO 1
<211> LENGTH: 14
<212> TYPE: PRT
<213> ORGANISM: Artificial Sequence
<220> FEATURE:
<223> OTHER INFORMATION: peptide analog

<400> SEQUENCE: 1

Cys Asn Arg Leu Asn Arg Ala Pro Gln Pro Asp Glu Leu Tyr
 1               5                  10

<210> SEQ ID NO 2
<211> LENGTH: 16
<212> TYPE: PRT
<213> ORGANISM: Artificial Sequence
<220> FEATURE:
<223> OTHER INFORMATION: peptide analog

<400> SEQUENCE: 2

Tyr Thr Thr Pro Glu Pro Ser Glu Leu Asp Asp Glu Asp Phe Arg Cys
 1               5                  10                  15

<210> SEQ ID NO 3
<211> LENGTH: 16
<212> TYPE: PRT
<213> ORGANISM: Artificial Sequence
<220> FEATURE:
<223> OTHER INFORMATION: peptide analog
```

```
-continued

<400> SEQUENCE: 3

Lys Arg Val Asp Ala Asp Ala Asp Pro Arg Gln Tyr Ala Asp Thr Cys
1               5                   10                  15
```

USE OF ANTIBODIES TO BLOCK THE EFFECTS OF GRAM-POSITIVE BACTERIA AND MYCOBACTERIA

This is a continuation of U.S. application Ser. No. 08/307,931, filed Sep. 16, 1994, (abandoned), which is a CIP of U.S. application Ser. No. 07/990,378, filed Dec. 15, 1992, (abandoned).

STATEMENT OF GOVERNMENT RIGHTS

This invention was supported in part by grant Nos. AI15136, GM28485 HL23586, and GM37696 from the U.S. National Institute of Health. The United States Government may have a significant interest in this invention.

BACKGROUND OF THE INVENTION

1. Field of the Invention

The present invention relates to methods and compositions for preventing or treating disease states caused by bacteria. More particularly, the present invention relates to antibodies and molecules that mediate cellular activation in response to Gram-positive bacteria and mycobacteria.

2. Description of Related Art

Septic shock is a tragic complication of bacterial infections, characterized by refractory hypotension, leading to inadequate organ perfusion, multiple organ failure and frequently death (Glauser, et al., *Lancet*, 338:732–736, 1991; Bone, *Chest*, 100:802–808, 1991). The lipopolysaccharide (endotoxin, LPS) of Gram-negative bacteria triggers cellular and physiological responses such as those observed during Gram-negative sepsis (Glauser, et al., supra; Ulevitch and Tobias, *Curr. Opin. Immunol.* 6:125–130, 1994). Cells of the immune/inflammatory systems respond to LPS by a pathway involving both plasma and membrane proteins (Ulevitch and Tobias, supra, 1994; Tobias, et al., *Am. J Respir. Cell Mol. Biol.*, 7:239–245, 1992). Included in this group of proteins are lipopolysaccharide-binding protein (LBP), a soluble serum protein which binds LPS and subsequently enables the binding of LPS to a second molecule, CD14. The LBP/CD14-dependent pathway is operative under physiological conditions and controls cell activation when nanomolar concentrations of LPS are used (Schumann, et al., *Science*, 249:1429–1433, 1990; Wright, et al., *Science*, 249:1431–1433, 1990). CD14 is found as a glycosylphosphatidylinositol-anchored membrane protein (mCD14) of myeloid cells, or in plasma/serum as a soluble protein (sCD14) (Ulevitch and Tobias, supra, 1994; Tobias, et al., supra, 1992; Pugin, et al., *Proc. Natl. Acad. Sci. USA*, 90:2744–2748, 1993a). Binding of LPS to mCD14 leads to cellular activation and generation of various proinflammatory molecules (Ulevitch and Tobias, supra, 1994). Other cell types such as endothelial, epithelial, vascular smooth muscle cells, and astrocytes do not bear CD14 but respond to soluble CD14-LPS complexes (Pugin, et al., supra, 1993a; Frey, et al., *J. Exp. Med.*, 176:1665–1671, 1992). A CD14- and LBP-independent pathway of LPS stimulation is observed only when high LPS concentrations are used.

In recent multicenter trials on sepsis, Gram-positive bacteria were found responsible for half of the cases of bacterial sepsis (Bone, *Arch. Intern. Med.*, 154:26–34, 1994). The prevalence of sepsis due to Gram-positive bacteria has risen markedly over the past two decades, and those microorganisms may well predominate as the cause of sepsis within the next few years (Bone, supra, 1994; Schaberg, et al., *Am. J. Med.*, 91:72S–75S, 1991). In contrast to what has been learned about how LPS stimulates cells much less is known about the molecular mechanisms of cellular activation by Gram-positive bacteria. Products of Gram-positive bacteria that can activate host cells include soluble exotoxins and cell wall components (Bone, supra, 1994). It is known that cell walls isolated from different Gram-positive strains, as well as purified cell wall components such as peptidoglycan or lipoteichoic acid activate cells of myeloid origin and induce cell responses very similar to that of LPS (Chin and Kostura, *J. Immunol.*, 151:5574–5585, 1993; Mattson, et al., *FEMS Immun. Med. Microbiol.*, 7:281–288, 1993; Rotta, Z. *Immunol.—Forsch, Bd.*, 149-230–244, 1975). However, few studies have addressed the mechanisms of receptor-dependent recognition of Gram-positive cell wall components by mammalian cells.

The hypothesis of pattern-recognition receptors advanced by Janeway (*Today*, 13:11–16, 1992) suggests that common cellular recognition pathways might be involved in responses to molecules with similar structural features from a variety of pathogens. There are currently no data to support this hypothesis except a report that lipoarabinomannan (LAM) from *Mycobacterium tuberculosis* activated a human monocytic cell line by CD14-dependent mechanisms (Zhang, et al., *J. Clin. Invest.*, 91:2076–2083, 1993). In addition, the group of Espevik, et al. (*Eur. J. Immunol.*, 23:255–261, 1993; Otterlei, et al., *Infect. Immun.*, 61:1917–1925, 1993) identified S1-4 linked polyuronic acid polymers from different origins, including Pseudomonas species, capable of stimulating human monocytes in a CD14-dependent manner. However, a recent study suggested that release of tumor necrosis factor (TNF) by human peripheral blood monocytes stimulated with large amounts of Gram-positive cell wall components was not inhibited by a monoclonal antibody to human CD14, MY4, that does block LPS-induced TNF release under some experimental conditions (Heumann, et al., *Infect. Immun.*, 69:2715–1721, 1994).

To explore in more detail the role of mCD14 or sCD14 in mediating cellular responses to cell wall preparations from Gram-positive organisms and to mycobacterial LAM, responses of CD14-positive and CD14-negative cell lines to these agonists in the presence and absence of anti-CD14 antibodies were compared. Evidence for a CD14 dependent activation of cells by gram-positive cell wall preparations and by LAM is shown. These data provide new information about pathways of cell activation used by Gram-positive bacteria and mycobacteria and lend support to the concept of pattern recognition receptors in cells of the immune system.

Current concepts support the contention that the primary response of the host to LPS (including man) involves the recognition of LPS by cells of the monocyte/macrophage lineage, followed by the rapid elaboration of a variety of cell products including the general group known as cytokines. Other cell types believed to participate in sepsis and in particular in the response to LPS are polymorphonuclear leukocytes and endothelial cells; each of these cell types are also capable of responding to LPS with the elaboration of potent inflammatory substances.

LPS is believed to be a primary cause of death in humans during gram-negative sepsis, particularly when the symptoms include adult respiratory distress syndrome (ARDS) (van Deventer, et al., *Lancet*, 1:605, 1988; Ziegler, et al., *J. Infect. Dis.*, 136:19–28, 1987). For instance, one particular cytokine, tumor necrosis factor alpha/cachectin (TNF), has recently been reported to be a primary mediator of septic shock (Beutler, et al., *N. Eng. J. Med.*, 316:379, 1987). Intravenous injection of LPS endotoxin from bacteria into experimental animals and man produces a rapid, transient release of TNF (Beutler, et al., *J. Immunol.*, 135:3972, 1985; Mathison, et al., *J. Clin. Invest.*, 81:1925, 1988). Evidence that TNF is a critical mediator of septic shock comes primarily from experiments in which pretreatment of animals with anti-TNF antibodies reduces lethality (Beutler, et al., *Science,* 229:869, 1985; Mathison, et al., *J. Clin. Invest.,* 81:1925, 1988). These reports suggest that interruption of the secretion of TNF caused by LPS or other factors would ameliorate the often lethal symptoms of sepsis.

Upon introduction of LPS into the blood, it may bind to a protein termed lipopolysaccharide binding protein (LBP). LBP is a 60 kD glycoprotein present at concentrations of less than 100 ng/ml in the serum of healthy animals and man. During the acute phase, LBP is synthesized by hepatocytes, and reaches concentrations of 30–50 ug/ml in serum. LBP can be purified from acute phase human and rabbit serum (Tobias, et al., *J. Exp. Med.,* 164:777–793, 1986). LBP recognizes the lipid A region of LPS and forms high affinity, 1:1 stoichiometric complexes with both rough and smooth form LPS (Tobias, et al., 264:10867–10871, 1989). LBP bears N-terminal sequence homology with the LPS-binding protein known as bactericidal permeability-increasing factor, (BPI) (Tobias, et al., supra, 1988). BPI is stored in the specific granules of PMN (Weiss, et al., *Blood,* 69:652–659, 1987) and kills gram negative bacteria by binding LPS and disrupting the permeability barrier (Weiss, et al., *J. Immunol.,* 132:3109–3115, 1984). In contrast to BPI, LBP is not directly cytotoxic for Gram-negative bacteria (Tobias, et al., *J. Biol. Chem.,* 263:13479–13481, 1988) and its precise biological function has been obscure.

By way of further background, the cells of the monocyte/macrophage lineage perform diverse immune function including the phagocytosis of microorganisms, the uptake of antigenic material and its presentation in a form which is stimulatory to helper T cells. They are probably also involved in the immune surveillance against tumors and they secrete some complement components and cytokines. Surface membrane antigens play a critical role in regulating these activities. Several monocyte/macrophage surface antigens have been identified and their molecular weight has been determined. One such antigen, CD14, is a 55-kD glycoprotein expressed by monocytes, macrophages, and activated granulocytes. It is recognized by a number of monoclonal antibodies (mAbs) including MO2, MY4, 3C10 and LEUM3. Although no biological function has yet been ascribed to CD14, its restricted expression on mature cells suggests an important effector function. The nucleotide sequence of the gene encoding the monocyte cell surface differentiation antigen CD14 has been determined and the amino acid residue sequence of CD14 has been deduced therefrom (Ferrero, et al., *Nucleic Acids Research Vol.,* 16:4173, 1988).

BRIEF SUMMARY OF THE INVENTION

A primary regulator of cytokine production and release is the CD14 receptor, particularly in cells of the monocyte/macrophage lineage. Inasmuch as cytokines secretion plays an important role in producing the symptoms of sepsis, the present invention contemplates methods and agents for inhibiting the secretion of cytokines, particularly TNF.

Therefore, in one embodiment, the present invention contemplates administering anti-CD14 antibody, preferably intravenously, to a patient at risk for or suffering from the symptoms of sepsis or other conditions resulting from exposure to bacterial toxins such as LPS, Gram-positive bacterial toxigenic cell wall components, or LAM from mycobacteria that induce cytokine secretions.

Therefore, in one embodiment of the invention a method is provided for treatment of symptoms associated with infection by Gram-positive bacteria and mycobacteria and toxemia associated with Gram-positive toxigenic cell wall components comprising administration of a therapeutically effective amount of an anti-CD14 antibody that blocks secretion of cytokines and blocks binding of cell wall components to CD14. The method can be practiced alone or in combination with the substantially simultaneous administration of other therapeutic modalities known to prevent or ameliorate the symptoms of sepsis, including treatment with one or more of an antibiotic, steroids, anti-TNF antibody, TNF antagonist and the like.

Further contemplated by the present invention are therapeutic compositions, typically in unit dose form, useful for preventing or ameliorating the symptoms of bacteremia associated with infection by Gram-positive bacteria and mycobacteria, and toxemia associated with Gram-positive toxigenic cell wall components, such as sepsis. The compositions comprise a pharmaceutically acceptable carrier containing one or more of an anti-CD14 antibody, or fragment thereof that inhibits production of cytokines and inhibits binding of cell wall components to CD14 as an active ingredient. In preferred embodiments, a therapeutic composition of this invention further contains, as active ingredients an agent known to prevent or ameliorate the symptoms of sepsis, such as an antibiotic, steroid, anti-TNF antibody, a TNF antagonist, soluble CD14 and the like, either alone, in sub-combination or combination.

BRIEF DESCRIPTION OF THE DRAWINGS

In the Figures forming a portion of the disclosure of this invention:

FIG. 3 illustrates that MO do not recognize LBP in the absence of LPS. E coated with biotin and streptavidin alone (EBAV) were incubated with Biotinylated LBP to yield ELBP. Both ELBP and EBAV were incubated with graded doses of LPS for 20 min at 37° C., washed, and binding to monolayers of MO was measured.

FIG. 11A is a graph showing nitrite production by murine macrophage cell line J774 stimulated with E. coli O111:B4 LPS. LPS only=open circles; LPS plus 0.25 mg/ml anti-murine CD14 IgG=closed triangles.

FIG. 11B is a graph showing nitrite production by murine macrophage cell line J774 mutant LR9 cells stimulated with E. coli O111:B4 LPS. LPS only=open circles; LPS plus 0.25 mg/ml anti-murine CD14 IgG=closed triangles.

FIG. 11C is a graph showing nitrite production by murine macrophage cell lines J774 stimulated with B. subtilis cell walls. Cell walls only=open circles; cell walls plus 0.25 mg/ml anti-murine CD14 IgG=closed triangles.

FIG. 11D is a graph showing nitrite production by murine macrophage cell line J774 mutant LR9 cells stimulated with B. subtilis cell walls. Cell walls only=open circles; cell walls plus 0.25 mg/ml anti-murine CD14 IgG=closed triangles.

DETAILED DESCRIPTION OF THE INVENTION

A. Definitions

Figure 1:
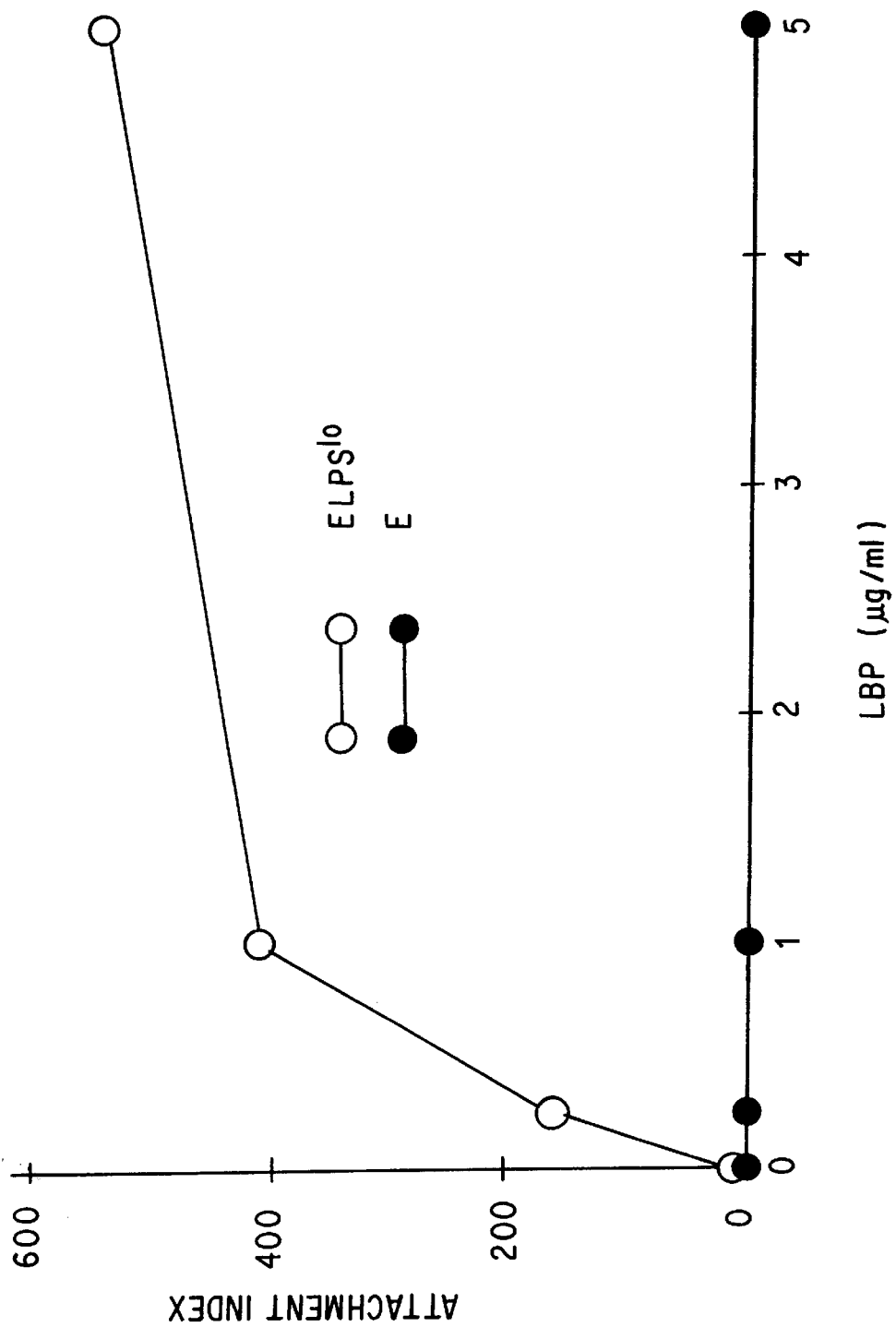
FIG. 1 illustrates that LBP enhances the interaction of ELPS with MO. Monolayers of MO were incubated with E or ELPS$^{lo}$ in the presence of varying doses of LBP, and attachment index was scored. A control acute phase protein, mannose binding protein (MBP) (5 ug/ml) caused no enhancement of binding of ELPS$^{lo}$ (attachment index 4.9). Results are representative of 4 separate experiments.

Amino Acid Residue: The amino acid residues described herein are preferred to be in the "L" isomeric form. However, residues in the "D" isomeric form can be substituted for any L-amino acid residue, as long as the desired functional property of immunoglobulin-binding is retained by the polypeptide. NH2 refers to the free amino group present at the amino terminus of a polypeptide. C00H refers to the free carboxy group present at the carboxy terminus of a polypeptide. In keeping with standard polypeptide nomenclature (*J. Biol Chem.*, 243:3552–59, 1969), abbreviations for amino acid residues are shown in the following Table of Correspondence:

TABLE OF CORRESPONDENCE

| SYMBOL 1-Letter | AMINO ACID 3-Letter | |
|---|---|---|
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Try | tryptophan |
| R | Arg | arginine |
| D | Asp | aspartic acid |
| N | Asn | asparagine |
| C | Cys | cysteine |

It should be noted that all amino acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino acid residues.

The term "antibody" in its various grammatical forms refers to a composition containing immunoglobulin molecules and/or immunologically active portions of immunoglobulin molecules, i.e., antibody fragments or molecules that contain an antibody combining site or paratope. In preferred embodiment, the antibodies used herein have been affinity purified.

An "antibody combining site" is that structural portion of an antibody molecule comprised of heavy and light chain variable and hypervariable regions that specifically binds antigen.

The phase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papin and pepsin, respectively, on substantially intact antibody molecules by methods that are well known. See for example, U.S. Pat. No. 4,342,566 to Theofilopolous, et al. (the disclosures of the art cited herein are hereby incorporated by reference). Fab' antibody molecule portions are also well known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred, and is utilized as illustrative herein.

The phrase "monoclonal antibody" in its various grammatical forms refers to an antibody containing having only one species of antibody combining site capable of immunoreacting with a particular antigen. A monoclonal antibody, thus, typically displays a single binding affinity for any antigen with which it immunoreacts. A monoclonal antibody may therefore contain an antibody molecule having a plurality of antibody combining sites, each immunospecific for a different antigen, e.g., a bispecific (chimeric) monoclonal antibody.

The phrase "substantially simultaneously" is used herein to mean within a time period sufficient to produce concurrent results, e.g., bacterial lysis as a result of antibiotic administration and amelioration or prevention of symptoms of sepsis that may occur as a result of that lysis by administration of an anti-CD14 antibody, anti-LBP antibody, LBP peptide analog, or a subcombination or combination thereof, as described herein.

The phrase "pharmaceutically acceptable" refers to molecular entities and compositions that are physiologically tolerable and do not typically produce an allergic or similar untoward reaction, such as gastric upset, dizziness and the like, when administered to a human.

B. Therapeutic Methods

The present invention contemplates methods of treating and/or preventing one or more of the symptoms of diseases such as sepsis, associated with infection by bacteria, particularly those associated with a transient increase in the blood level of TNF, such as fever, hypotension, neutropenia, leukopenia, thrombocytopenia, shock and multiple organ failure. Patients in need of such treatment include those at risk for or suffering toxemia, such as endotoxemia resulting from a Gram-negative, Gram-positive bacterial or mycobacterial infection or toxemia, serpent venom poisoning, hepatic failure, and the like. In addition, some patients having viral or fungal infection display the symptoms of sepsis and may benefit from a therapeutic method of this invention. Patients particularly able to benefit from the present invention are those suffering infection by *E. coli, Haemophilus influenza* B, *Neisseria meningitides,* staphylococci, or pneumococci. Patients at risk for sepsis include those suffering burns, gunshot wounds, renal or hepatic failure due to chemical poisoning or abuse, and the like.

Thus, in one embodiment, the present invention contemplates a method of ameliorating one or more of the symptoms of sepsis or other conditions resulting from exposure to bacterial toxins such as LPS, Gram-positive bacterial toxigenic cell wall components, or LAM from mycobacteria that induce cytokine secretions by administering an anti-CD14 antibody, preferably intravenously, to a patient at risk for or suffering the symptoms of such diseases.

Therefore, in one embodiment of the invention a method is provided for treatment of symptoms associated with bacteremia and toxemia caused by Gram-positive bacteria and mycobacteria comprising administration of a therapeutically effective amount of an anti-CD14 antibody that blocks secretion of cytokines. The method can be practiced alone or in combination with the substantially simultaneous administration of other therapeutic modalities known to prevent or ameliorate the symptoms of sepsis and toxemia, including treatment with one or more of an antibiotic, steroids, anti-TNF antibody, TNF antagonist and the like.

Further contemplated by the present invention are therapeutic compositions, typically in unit dose form, useful for preventing or ameliorating the symptoms of infectious conditions, such as bacteremia, sepsis, and other forms of toxemia, caused by Gram-negative bacteria, Gram-positive bacteria and mycobacteria (an acid-fast type of Gram-positive bacteria). The compositions comprise a pharmaceutically acceptable carrier containing as an active ingredient one or more of an anti-CD14 antibody, or fragment thereof, that inhibits production of cytokines. In preferred embodiments, a therapeutic composition of this invention further contains, as active ingredients an agent known to prevent or ameliorate the symptoms of bacterial conditions and sepsis, such as an antibiotic, steroid, anti-TNF antibody, a TNF antagonist, soluble CD14 and the like, either alone, in sub-combination or combination.

The phrase "therapeutically effective amount" is used herein to mean an amount sufficient to prevent, and preferably reduce by at least about 30 percent, more preferably by at least 50 percent, most preferably by at least 90 percent, a clinically significant increase in the plasma level of TNF. Preferred therapeutically effective amounts for the agents used herein as active ingredients include those described in Section C. A clinically significant increase in the plasma level of TNF is an increase to at least about 25 pg/ml. Methods for determining the plasma TNF levels are well known in the art, particularly preferred methods being those described herein.

It should be noted that levels of TNF in normal healthy humans or in laboratory animals are estimated to be no more than about 10 pg/ml, a value that is at the limit of detection by the most sensitive assays for TNF (Michie, et al., *New Eng J. Med.*, 318:1481–1486, 1988; Mathison, et al.,*J. Clin. Invest.*, 81:1925, 1988; and Waage, et al., *Lancet*, 1:355–357,1987). Following exposure to LPS, the levels of TNF have been shown to rise 10–20 fold to levels of up to 400 pg/ml (vide supra). Recently a good correlation has been shown between serum TNF levels and fatal outcome in infection with Gram-negative, LPS-containing meningococcal bacteria (Waage, et al., supra, 1987). Further in animal models of sepsis with subhuman primates similar increases in TNF were noted and these changes were directly correlated with lethality (Tracey, et al., *Nature,* 330:662–664, 1987).

In another embodiment, the method comprises administering to a patient in need of treatment or at risk for Sepsis a therapeutically effective amount of an anti-CD14 antibody, preferably an amount sufficient to inhibit TNF secretion induced by LPS, Gram-positive toxigenic cell wall components, or LAM of mycobacteria in vivo by cells, such as cells of the monocyte/macrophage lineage, preferably monocyte-derived macrophages.

Preferably, the anti-CD14 antibody used in a therapeutic method of this invention is an affinity purified polyclonal antibody. More preferably, the antibody is a monoclonal antibody (mAb). In addition, it is preferable for the anti-CD14 antibody molecules used herein be in the form of Fab, Fab', F(ab')$_2$ or F(v) portions of whole antibody molecules.

Preferred monoclonal antibodies useful in practicing the present invention are those capable of being produced by a hybridoma such as 60b described in Ashman, et al. (*Blood,* 69:886–892, 1987), and most preferably by 3C10 (deposit number TIB22B at American Type Culture Collection, Rockville, Md.), described in Van Voorhis, et al. (*J. Exp. Med.,* 158:126–145,1983) and the like. While mAbs 60b and 3C10 can be produced by hybridoma culture, the invention is not so limited. Also contemplated is the use of mAbs produced by an anti-CD14 immunoglobulin expressing nucleic acid cloned from a hybridoma such as 60b and/or 3C10. That is, the nucleic acid expressing the anti-CD14 antibody molecules secreted by hybridoma 3C10 or the like can be transferred into another cell line to produce a transformant. The transformant is genotypically distinct from the original hybridoma, but is also capable of producing anti-CD14 antibody molecules, including immunologically active fragments of whole antibody molecules, corresponding to those secreted by the hybridoma. See, for example, U.S. Pat. No. 4,642,334 to Reading; PCT Publication No. WO 890099 to Robinson, et al.; European Patent Publications No. 0239400 to Winter, et al. and No. 0125023 to Cabilly, et al.

Preferred monoclonal antibodies display an immunoreactivity for CD14 that is similar to that of those produced by the above-described hybridomas. As used herein, the term "immunoreactivity" in its various grammatical forms refers to the concentration of antigen required to achieve a 50% inhibition of the immunoreaction between a given amount of the antibody and a given amount of CD14 antigen from LPS, Gram-positive toxigenic cell wall components, or from LAM of mycobacteria. That is, immunoreactivity is the concentration of antigen or toxigenic component required to achieve a $B/B_O$ value of 0.5, where $B_0$ is the maximum amount of antibody bound in the absence of competing antigen and B is the amount of antibody bound in the presence of competing antigen, and both $B_0$ and B have been adjusted for background (see, Robard, *Clin. Chem.,* 20:1255–1270, 1974).

In another embodiment, a therapeutic method of the present invention comprises administering a therapeutically effective amount of an anti-LBP antibody preferably an affinity-purified polyclonal antibody and more preferably a mAb. In addition, it is preferable for the anti-LBP antibody molecules used herein be in the form of Fab, Fab', F(ab')$_2$ or F$_{(v)}$ portions of whole antibody molecules. Preferably, the amount of anti-LBP antibody administered is sufficient to reduce by at least about 30 percent, preferably by at least 80 percent, an LBP-LPS complex induced clinically significant increase in the blood level of TNF in a patient displaying at least one of the symptoms of sepsis. As previously discussed, patients capable of benefiting from this method include those suffering endotoxemia as a result of a Gram-negative bacterial infection. Methods for isolating LBP and inducing anti-LBP antibodies are well known in the art. See, for example Tobias, et al. (*J. Exp. Med.,* 164:777–793, 1986). Methods for determining and optimizing the ability of an anti-LBP antibody to inhibit the binding of LBP-LPS complexes to CD14 and thereby inhibit LBP-induced TNF secretion, are well known in the art. For instance, an anti-LBP antibody can be substituted for the anti-CD14 antibody in the assay described in Example 16.

Preferred anti-LBP antibodies useful in practicing the present invention immunologically cross-react with a peptide analog of LBP. A "LBP peptide analog" is a polypeptide capable of competitively inhibiting the binding of LPS-LBP complexes to CD14 expressed on the surface of monocyte derived macrophages. Preferred LBP peptide analogs are those shown in Table I.

TABLE I

| Designation | Amino Acid Residue Sequence |
| --- | --- |
| C16Y | CNRLNRAPQPDELY (SEQ ID NO:1) |
| Y16C | YTTPEPSELDDEDFRC (SEQ ID NO:2) |
| K16C | KRVDADADPRQYADTC (SEQ ID NO:3) |

Methods for producing polyclonal anti-polypeptide antibodies are well known in the art. See U.S. Pat. No. 4,493,795 to Nestor, et al. A monoclonal antibody, typically containing Fab and/or F(ab')$_2$ portions of useful antibody molecules, can be prepared using the hybridoma technology described in Antibodies A Laboratory Manual, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with CD14 or an LBP-binding portion thereof, or LBP or a CD14-binding portion thereof, Alternatively the mammal can be hyperimmunized with toxigenic components from cells walls of Gram-positive bacteria, or LAM from mycobacteria, particularly CD14-binding portions thereof.

It is preferred that the myeloma cell line be from the same species as the lymphocytes. Typically, a mouse of the strain 129 GIX$^+$ is the preferred mammal. Suitable mouse myelomas for use in the present invention include the hypoxanthine-aminopterin-thymidine-sensitive (HAT) cell lines P3X63-Ag8.653, and Sp2/0-Ag14 that are available from the American Type Culture Collection, Rockville, Md., under the designations CRL 1580 and CRL 1581, respectively.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact with CD14 or LBP and their ability to inhibit LPS-induced TNF secretion using the method described in Example 16.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well known techniques.

Media useful for the preparation of these compositions are both well known in the art and commercially available and include synthetic culture media, inbred mice and the like. An exemplary synthetic medium is Dulbecco's minimal essential medium (DMEM; Dulbecco, et al., *Virol.*, 8:396, 1959) supplemented with 4.5 gm/l glucose, 20 mm glutamine, and 20% fetal calf serum. An exemplary inbred mouse strain is the Balb/c.

Methods for producing monoclonal anti-polypeptide antibodies are also well known in the art (see Niman, et al., *Proc. Natl. Acad. Sci. USA*, 80:4949–4953, 1983). Typically, one or more of LBP peptide analog is used either alone or conjugated to an immunogenic carrier, as the immunogen in the before described procedure for producing anti-CD14 monoclonal antibodies. The hybridomas are screened for the ability to produce an antibody that immunoreacts with the LBP peptide analog and LBP or with the CD14-binding portion of Gram-positive bacterial cell walls (the toxigenic components) or LAM from mycobacteria.

The ability to inhibit LPS-LBP complex binding to CD14 by mAbs demonstrating the appropriate immunologic cross-reacting is confirmed using the assay of Example 16.

In another embodiment, a therapeutic method of the present invention involves administering a therapeutically effective amount of a LBP peptide analog, preferably an analog having a sequence as shown in Table I.

Patients at risk for or exhibiting the symptoms of sepsis are capable of benefiting from the administration of therapeutic modalities known in the art to prevent or ameliorate those symptoms. Thus, the present invention contemplates administering a therapeutically effective amount of an anti-CD14 antibody, anti-LBP antibody, LBP peptide analog, a subcombination or combination thereof, substantially simultaneously with therapeutic administration of a modality known to prevent or treat the symptoms of sepsis. For instance, intervention in the role of TNF in sepsis, either directly or indirectly, such as by use of an anti-TNF antibody and/or a TNF antagonist, can prevent or ameliorate the symptoms of sepsis. Particularly preferred is the use of an anti-TNF antibody as an active ingredient, such as a monoclonal antibody having an immunologic specificity for TNF corresponding to that described by (Tracey, et al, *Nature*, 330:662–664, 1987).

Similarly, a therapeutic method of this invention can further include substantially simultaneous treatment with a steroid, such as cortisol, hydrocortisone and the like.

A patient exhibiting the symptoms of sepsis is usually treated with an antibiotic, typically an aminoglycoside such as gentamycin or a beta-lactim such as penicillin, cephalosporin and the like. Thus, a preferred therapeutic method includes administering a therapeutically effective amount of an anti-CD14 antibody, anti-LBP antibody, LBP peptide analog subcombination or combination thereof as described herein, substantially simultaneously with administering a bactericidal amount of an antibiotic. The phrase "bactericidal amount" is used herein to mean an amount sufficient to achieve a bacteria-killing blood concentration in the patient receiving the treatment. The bactericidal amount of antibiotics generally recognized as safe for administration to humans is an amount well known in the art and varies, as is also well known, with the antibiotic and the type of bacterial infection being treated.

In preferred embodiments, administration of an anti-CD14 antibody, anti-LBP antibody, LBP peptide analog or combination thereof as described herein occurs within about 48 hours, preferably within about 12–36 hours, more preferably within about 2–8 hours and most preferably substantially concurrently with administration of the antibiotic.

Antibiotics useful in practicing the present invention include those antibiotic, antibacterial and antiseptic agents having formulations described in the Physicians' Desk Reference, Huff, B. B. ed., Medical Economics Company, Inc., Oradell, N.J. (1989). In another embodiment, the present invention contemplates administering a therapeutically effective amount of CD14, preferably a soluble portion thereof that binds LPS-LBP complexes, alone or in subcombination or combination with a therapeutically effective amount of an anti-TNF antibody, an anti-LBP antibody, and an antibiotic. The cDNA coding for CD14 and its deduced amino acid residue sequence are well known in the art. See Goyert, et al., *Science*, 239:497–500 1988; Ferrero, et al., *Nuc. Acids Res.*, 16:4173, 1988; and Bazil, et al., *Eur. J. Immunol.*, 16:1583–1589, 1986.

C. Therapeutic Compositions

The present invention further contemplates therapeutic compositions useful in practicing the therapeutic methods of this invention. A subject therapeutic composition includes, in admixture, a pharmaceutically acceptable excipient (carrier) and one or more of an anti-CD14 antibody, anti-LBP antibody, and LBP polypeptide analog as described herein as an active ingredient. In preferred embodiments, the composition comprises an anti-CD14 mAb capable of inhibiting the binding of LPS-LBP complexes to CD14. A preferred mAb is 60b, and more preferably is 3C10. For treatment of sepsis or other disease states associated with production of cytokines caused by Gram-positive bacteria or mycobacteria, the preferred monoclonal antibodies are 63D3 mAB produced by hybridoma cell line ATCC# HB44 or 28C5 produced by hybridoma cell ATCC# HB 11364. Hybridoma cell line HB44 is with publicly available through American Type Culture Collection, 1301 Parklawn Drive, Rockville, Md., U.S.A., on May 27, 1993, under the terms of the Budapest Treaty. The deposit was made under the provisions of the Budapest Treaty on the International Recognition of the Deposit of Microorganisms for the Purpose of Patent Procedure and the Regulations thereunder (Budapest Treaty). This assures maintenance of viable cultures for 30 years from the date of deposit. The organisms will be made available by ATCC under the terms of the Budapest Treaty and Applicant assures permanent and unrestricted availability of the progeny of the culture to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

In another preferred embodiment, the compositions comprise an anti-LBP antibody, preferably a mAb, that inhibits the binding of LPS-LBP complexes to CD14. Particularly preferred are compositions wherein the anti-LBP antibody immunoreacts with a LBP peptide analog having a sequence shown in Table I.

A preferred composition comprises a LBP peptide analog that acts as an antagonist to LPS-LBP complexes in binding to CD14. Preferred LBP peptide analogs for use in compositions of this invention are those having a sequence shown in Table I.

Preferred therapeutic compositions further include an effective amount of one or more of the following active ingredients: an antibiotic, a steroid, and anti-TNF antibody and a TNF antagonist. Exemplary formulations are given below:

| Ingredient | Dose (mg/ml) |
|---|---|
| Formulation A | |
| gentamicin (sulfate) | 40 |
| Anti-CD14 (mAb 3C10) | 10 |
| sodium bisulfite USP | 3.2 |
| disodium EDTA USP | 0.1 |
| water for injection q.s.a.d. | 1.0 ml |
| Formulation B | |
| anti-TNF antibody | 10 |
| anti-CD14 (mAb 3C10) | 10 |
| sodium bisulfite USP | 3.2 |
| disodium EDTA USP | 0.1 |
| water for injection q.s.a.d. | 1.0 ml |
| Formulation C | |
| gentamicin (sulfate) | 40 |
| anti-TNF antibody | 10 |
| anti-CD14 (mAb 3C10) | 10 |
| sodium bisulfite USP | 3.2 |
| disodium EDTA USP | 0.1 |
| water for injection q.s.a.d. | 1.0 ml |

In another embodiment, the present invention contemplates a therapeutic composition useful in treating sepsis comprised of CD14 or a LBP-binding soluble portion thereof in a pharmaceutically acceptable carrier. Preferably, the composition further includes a therapeutically effective concentration of one or more of an anti-TNF antibody, an anti-LBP antibody and an antibiotic.

The preparation of therapeutic compositions which contain polypeptides or antibody molecules as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide or antibody can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide- or antibody-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of CD14 or LPS-LBP complex binding capacity desired. Precise amounts of active ingredient required to be administered depend on the judgment of the practitioner and are peculiar to each individual. However, suitable dosage ranges are of the order of 0.1 to 20, preferably about 0.5 to about 10, and more preferably one to several, milligrams of active ingredient per kilogram bodyweight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nano molar to ten micromolar in the blood are contemplated.

As used herein, "pg" means picogram, "ng" means nanogram, "ug" means microgram, "mg" means milligram, "ul" means microliter, "ml" means milliliter, "l" means liter.

ANTI-MURINE CD14 ANTIBODY BLOCKS CELL ACTIVATION

In order to establish whether the anti-murine CD14 antibody blocked LPS-induced cell activation its effect on activation of murine monocytes/macrophages was first determined. A polyclonal IgG preparation of rabbit anti-murine CD14 inhibited LPS-induced TNF production in RAW cells and in mouse blood, whereas IgG from a nonimmune rabbit had no effect (data not shown). In experiments not shown here, LPS-dependent nitrite production by RAW and J774 cells was also blocked by the anti-murine CD14 IgG. The anti-CD14 antibody had no effect on TNF-induced production of nitrite in the same cells, demonstrating the specificity of inhibition with anti-CD14 antibody (not shown). F(ab')$_2$ IgG fragments of the anti-murine CD14 IgG inhibited in the same manner as intact antibody, eliminating any contribution of Fc domain interactions with the cell (not shown).

Figure 10A:
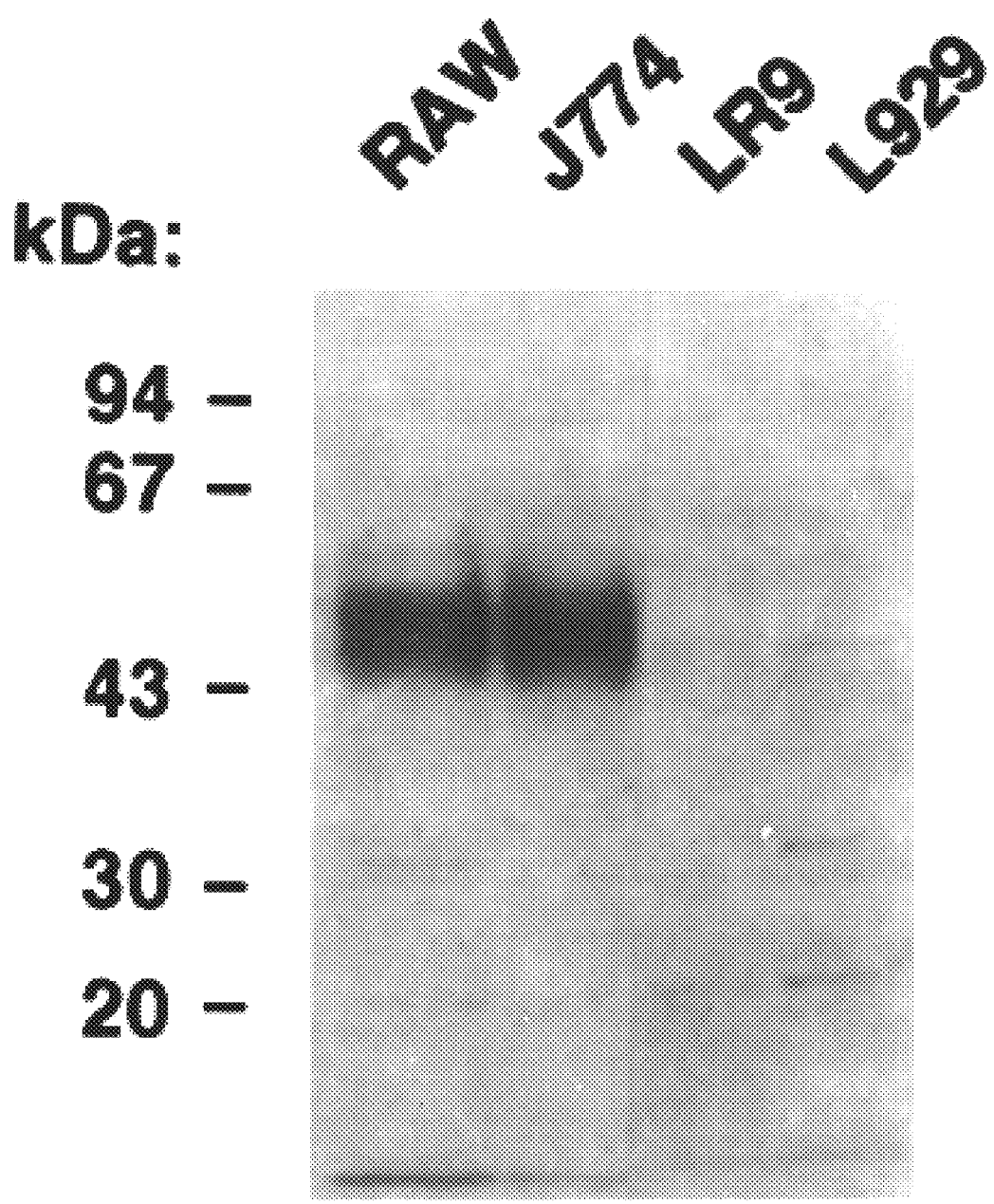
FIG. 10A is a Western blot of supernates from murine cells treated with phosphoinositol specific phospholipase C stained with rabbit anti-murine IgG prepared as described in Example 21. RAW=murine macrophage RAW cell line 264.7; J774=murine macrophage cell line J774; LR9=J774 mutant LR9 cells; L929=murine fibroblast L929 cells.
Figure 10B:
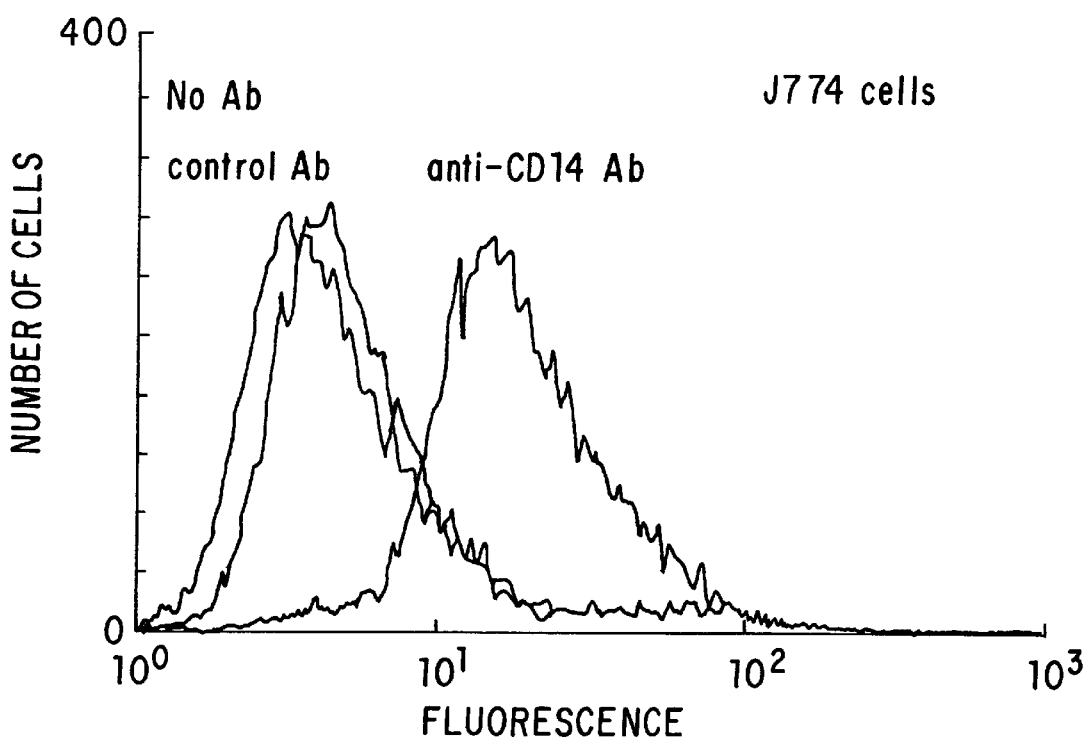
FIGS. 10B and 10C are graphs showing the results of FACS analysis of J774 and LR9 cells immunoreacted with F(ab')$_2$ fragments from a rabbit antimurine CD14 IgG antibody or control F(ab')$_2$ IgG fragments from a nonimmune rabbit using a FITC-goat anti-rabbit secondary antibody.
Figure 10C:
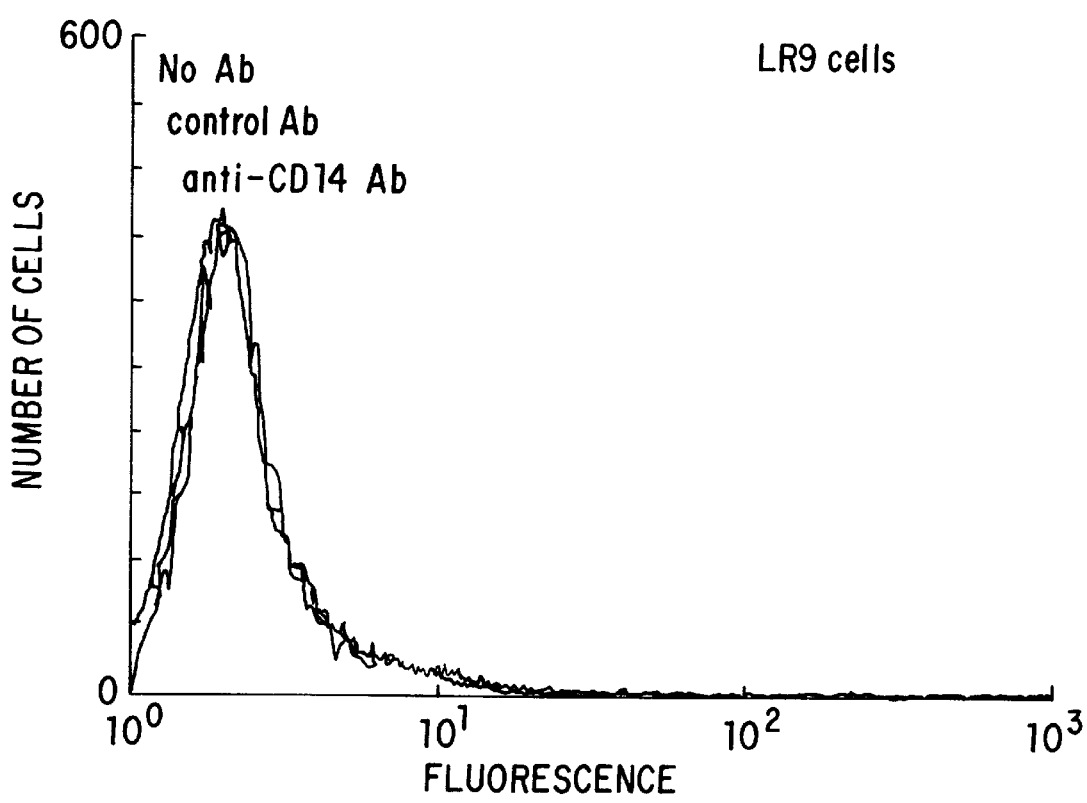
Figure 12B:
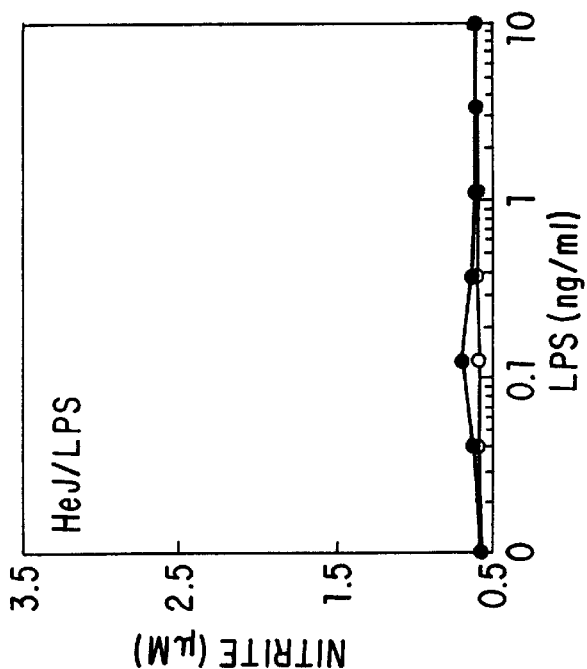
FIG. 12B is a graph showing nitrite production by murine peritoneal elicited macrophages from C3H/HeJ mouse strain in response to E. coli O111:B4 LPS. LPS only=open circles; LPS plus 0.25 mg/ml anti-murine CD14 IgG=closed triangles.
Figure 12A:
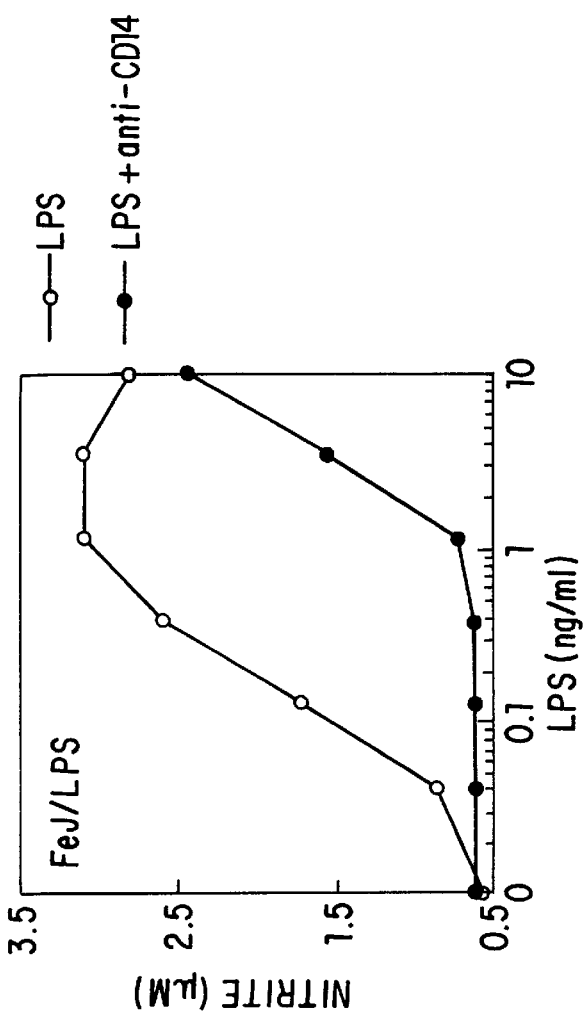
FIG. 12A is a graph showing nitrite production by murine peritoneal elicited macrophages from C3H/FeJ mouse strain in response to E. coli O111:B4 LPS. LPS only=open circles; LPS plus 0.25 mg/ml anti-murine CD14 IgG=closed circles.
Figure 12D:
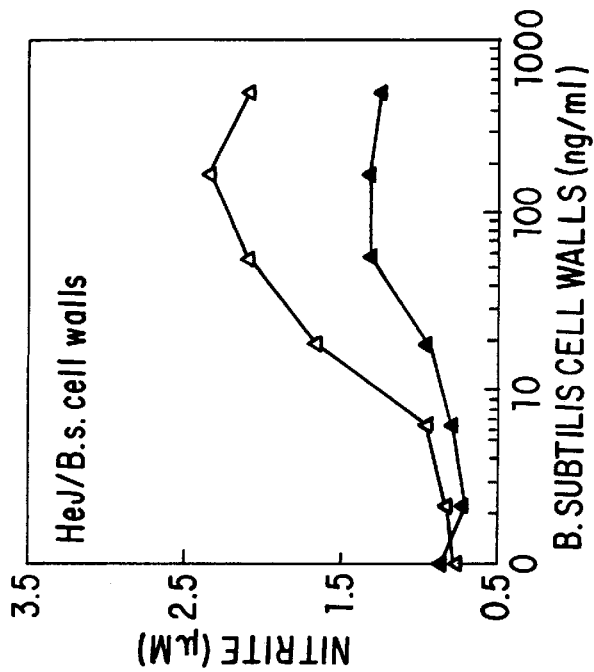
FIG. 12D is a graph showing nitrite production by murine peritoneal elicited macrophages from C3H/HeJ mouse strain in response to B. subtilis cell walls. Agonist only=open circles; agonist plus 0.25 mg/ml anti-murine CD14 IgG=closed circles.
Figure 12C:
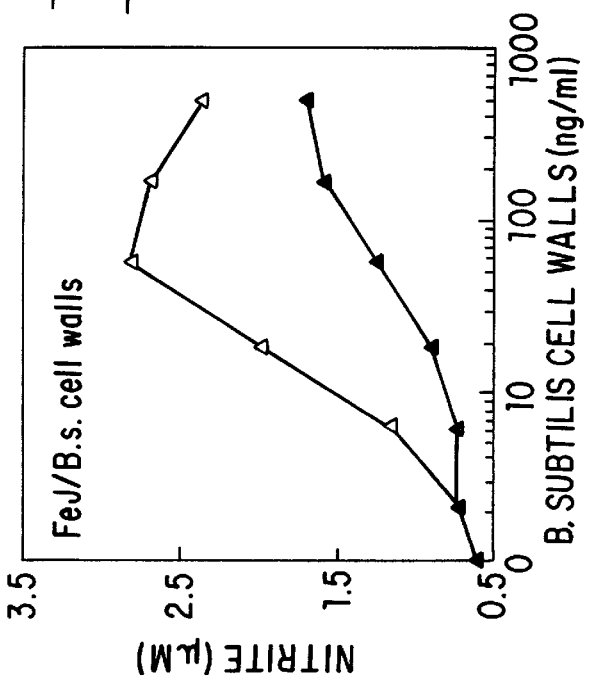
FIG. 12C is a graph showing nitrite production by murine peritoneal elicited macrophages from C3H/FeJ mouse strain in response to B. subtilis cell walls. Cell walls only=open triangles; cell walls plus 0.25 mg/ml anti-murine CD14 IgG=closed triangles.
Figure 12F:
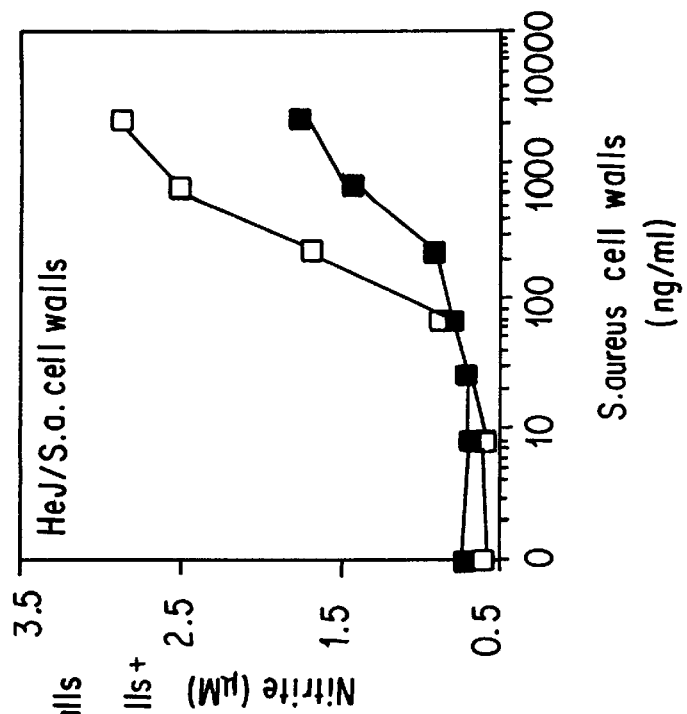
FIG. 12F is a graph showing nitrite production by murine peritoneal elicited macrophages from C3H/HeJ mouse strain in response to S. aureus cell walls. Agonist only=open circles; agonist plus 0.25 mg/ml anti-murine CD14 IgG=closed triangles.
Figure 12E:
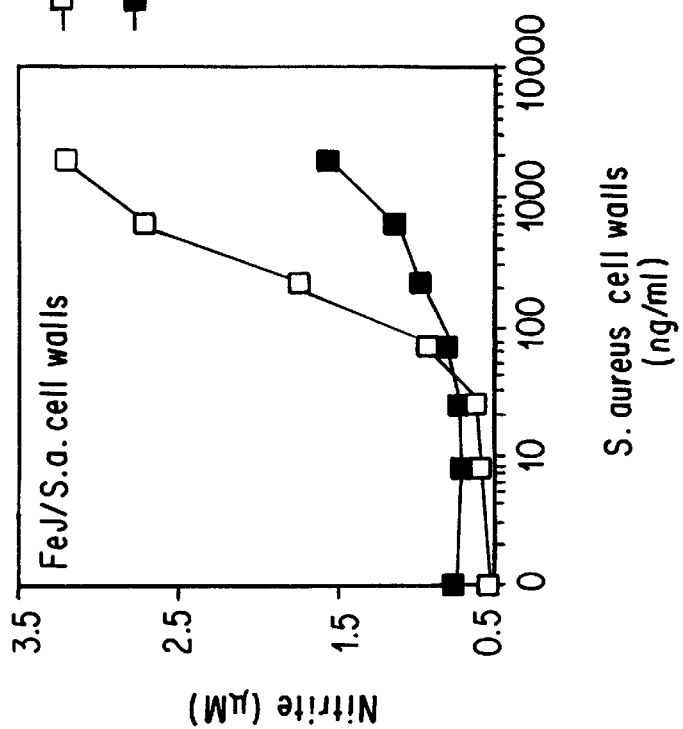
FIG. 12E is a graph showing nitrite production by murine peritoneal elicited macrophages from C3H/FeJ mouse strain in response to S. aureus cell walls. Agonist only=open squares; agonist plus 0.25 mg/ml anti-murine CD14 IgG=closed squares.

Results shown in FIG. 10 demonstrate that the polyclonal anti-murine CD14 antibody recognizes native murine CD14 and blocks LPS-induced cell activation occurring via CD14 (not shown). Based upon these findings, additional experiments were performed to test the hypothesis that CD14 might play a role in responses of murine macrophages to Gram-positive bacterial cell walls and LAM.

As shown in FIG. 11, it has been discovered that Anti-murine CD14 polyclonal antibody inhibited LPS- or *B. subtilis* cell wall-dependent nitrite production in J774 cells. The LR9 cells were markedly hyporesponsive to stimulation by either LPS or as shown in FIG. 11B, Gram-positive cell walls. Increasing the concentration of LPS to 3 ng/ml or cell walls to 1000 ng/ml did induce nitrite production in these cells, but under these experimental conditions administration of anti-CD14 antibody failed to reduce the response (FIG. 11). Similar data were obtained with cell walls from a group A Streptococcus strain (data not shown). PEM from C3H/FeJ (LPS-responsive mice) responded to LPS and to cell wall preparations from *B. subtilis* or *S. aureus* as shown in FIG. 12; anti-murine CD14 polyclonal antibody inhibited responses both to LPS and to cell walls. Not surprisingly PEM from C3H/HeJ mice, a strain known to be non-responsive to LPS) failed to respond to LPS, but did produce nitrite after treatment with cell wall preparations from two different Gram-positive microorganisms (FIG. 12). Dose response characteristics for cell wall preparations were very similar in PEM from the two different mouse strains. Another cell wall preparation from group B Streptococcus also stimulated nitrite production in PEM (not shown).

Quite unexpectedly, it was observed that cell wall-induced nitrite production by C3H/HeJ PEM was inhibited by anti-CD14 polyclonal antibody as shown in FIG. 12). In addition, GG2EE cells, macrophages derived from C3H/HeJ mice (Blasi, et al., 1987), were stimulated by LAM to produce a nitrite response that was blocked by anti-murine CD14 IgG (not shown).

CD14-independent pathways for stimulation by Gram-positive cell wall preparations or LPS are also found to be operative since the inhibitory effects of anti-CD14 were always overcome by increasing stimulus concentrations. Nevertheless, the totality of findings presented in FIGS. 11 and 12 support a prominent role for CD14 in responses to both LPS and Gram-positive cell walls such that therapeutic intervention by anti-CD14 antibodies can modify and ameliorate the toxic effects of both Gram-negative and Gram-positive bacteria in mammals.

RESPONSES IN CD14-POSITIVE AND CD14-NEGATIVE CELL LINES

Although the results obtained with J774 (CD14-positive) and LR9 (CD14-negative) cell lines suggest an important role for CD14 in responses to Gram-positive cell walls, these data have to be interpreted cautiously. Although the inventors herein have shown that LR9 cells lack CD14, because this line was selected from chemically mutagenized J774 cells, the full basis of LPS hyporesponsiveness is not known. Therefore, an additional series of experiments were performed using either THP-1 cells that express high levels of CD14 after treatment with 1,25 dihydroxyvitamin D3 (Tobias, et al., *J. Immunol.*, 150:3011–3021, 1993) or transfected 70Z/3 cells expressing human CD14 (Lee, et al., *Proc. Natl. Acad Sci. USA*, 90:9930–9934, 1993). Stimulation of THP-1 cells with LPS or Gram-positive toxigenic cell wall components to release IL-8 required prior treatment with vitamin D3 (not shown).

Figure 13A:
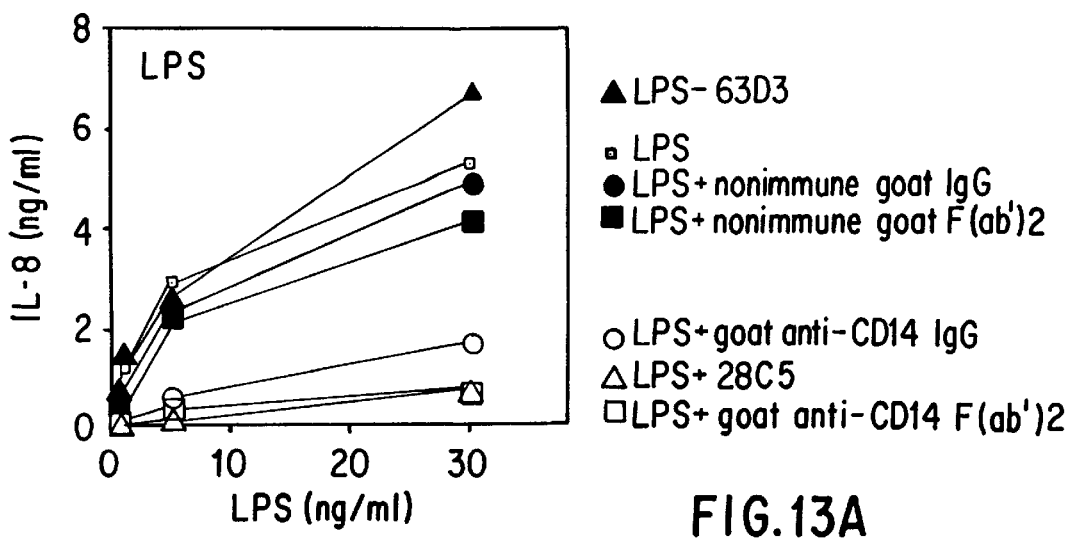
FIGS. 13(A–C) displays graphs showing secretion of IL-8 by 1,25 dihydroxy-vitamin D$_3$-differentiated THP-1 cells in response to E. coli O111:B4 LPS FIG. 13 (panel A), B. subtilis cell walls FIG. 13 (panel B), and mycobacterial lipoarabinomannan (LAM, FIG. 13 panel C). Antibodies added: no antibody=small dotted squares; 0.25 mg/ml goat anti-human CD14 IgG=open circles; 0.25 mg/ml nonimmune goat IgG=closed circles; 0.25 mg/ml goat anti-human CD14 F(ab')$_2$ IgG fragments=open squares; 0.25 mg/ml nonimmune goat F(ab')$_2$ IgG fragments=closed squares; 10 μg/ml anti-CD14 mAb 28C5=open triangles; 10 μg/ml anti-CD14 mAb 63D3=closed triangles.
Figure 13B:
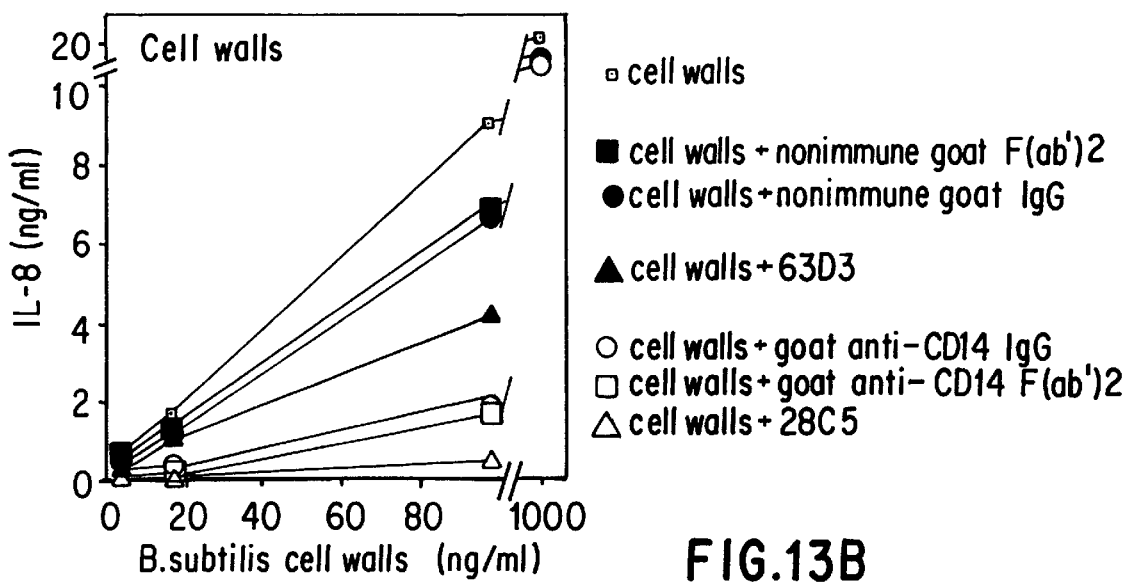
Figure 13C:
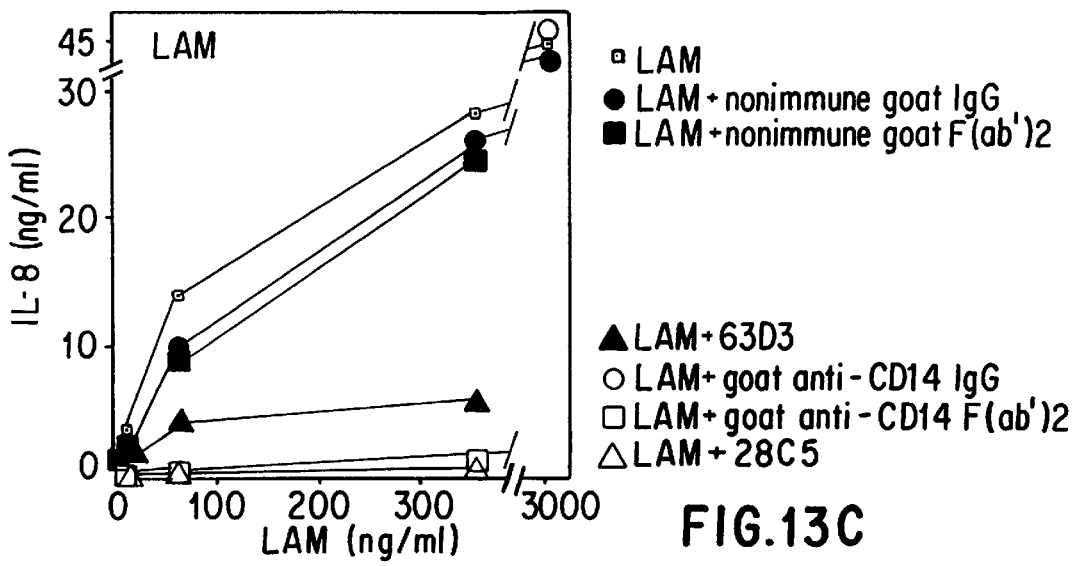

To determine the role of CD14 expression in these cells, various anti-human CD14 antibodies were tested for the ability to block cell activation. First the effects were compared of polyclonal and monoclonal antibodies to human CD14 on THP-1 activation by LPS, by Gram-positive cell wall preparations, and by LAM. As shown in FIG. 13, polyclonal anti-hCD14 antibody (IgG fraction or F(ab')$_2$ IgG fragments) blocked LPS-, Gram-positive cell wall-, and LAM-induced IL-8 release, while non-immune IgG or its F(ab')$_2$ fragments were without any effect. Monoclonal antibodies to human CD14, 63D3 (ATCC# HB44) and 28C5 (ATCC# HB 11364) were used to pretreat cells prior to addition of either LPS or Gram-positive cell wall preparations.

As shown in FIG. 13, mAB 28C5 blocked responses to LPS and to the cell wall preparations and to LAM. In contrast, mAB 63D3 did not inhibit LPS stimulation, but partially blocked stimulation by the cell wall material and by LAM. THP-1 cell activation by *B. subtilis* cell walls or LAM used at concentrations of 1–3 pg/ml could not be blocked by polyclonal anti-hCD14 antibodies (FIG. 13). THP-1 cell activation was observed to be CD14-dependent when the agonist concentration was in the nanogram/ml range. In other studies it was also determined that stimulation by cell wall preparation from *S. pneumoniae* also required CD14

(not shown) but stimulation of THP-1 cells with soluble peptidoglycan from S. aureus was not blocked by inclusion of anti-CD14 polyclonal IgG (not shown).

Figure 14A:
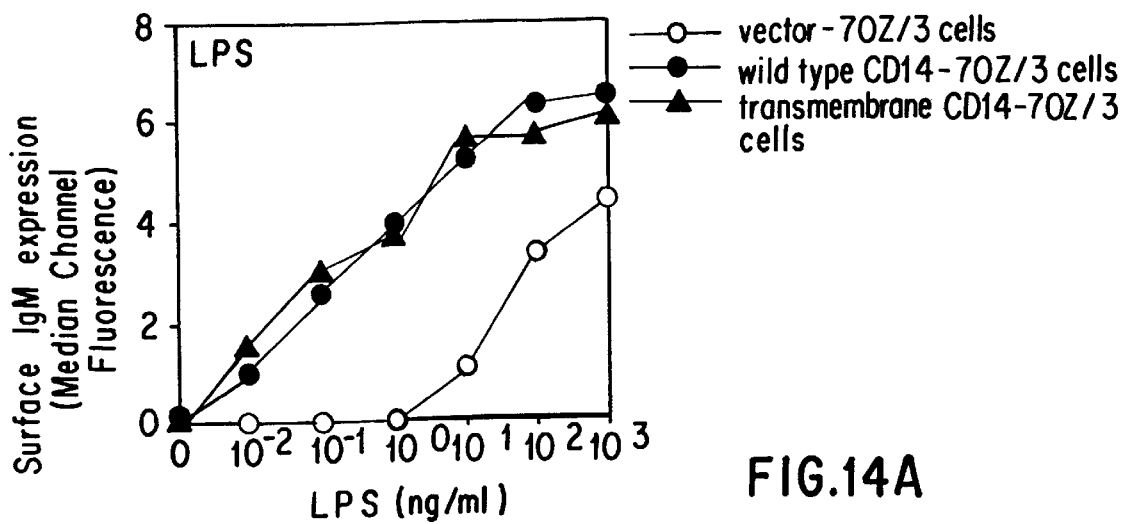
FIGS. 14(A–C) displays graphs showing the results of FACS analysis of surface IgM upregulation (expressed as median channel fluorescence in arbitrary units) by murine pre-B 70Z/3 cells in response to E. coli O111:B4 LPS FIG. 14 (panel A), B. subtilis cell walls FIG. 14 (panel B), and mycobacterial lipoarabinomannan (LAM, FIG. 14 panel C). Vector-transfected cells (open circles); wild type CD14-transfected cells (closed circles); transmembrane chimera CD14-transfected cells (closed triangles).
Figure 14B:
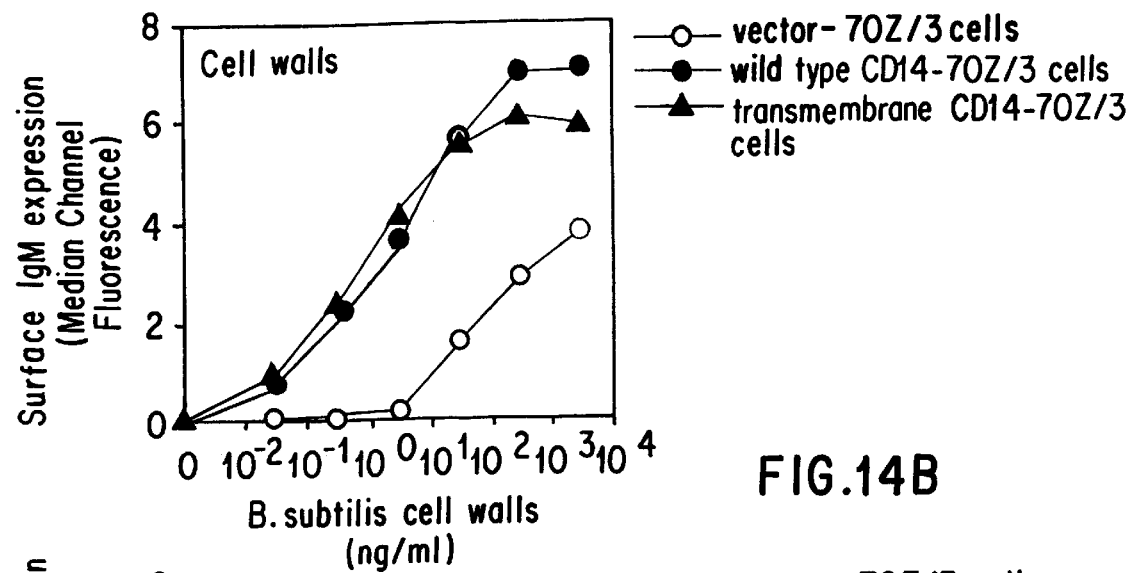
Figure 14C:
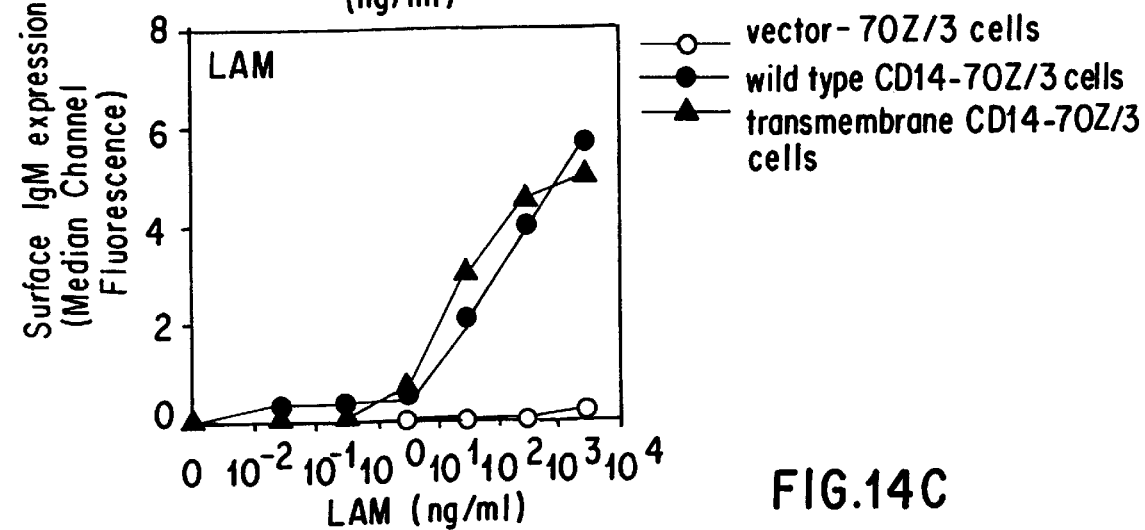

The effect of CD14 expression on LPS responses of a murine pre-B cell line, 70Z/3, has previously been described (Lee, et al., *J. Exp. Med.,* 175:1697–1705, 1992; Lee, et al., supra, 1993). 70Z/3 cells transfected with CD14 (70Z/3-hCD14 cells) behave similarly to macrophages with respect to LPS binding and early signalling events (Lee, et al., supra, 1993). These cells permit a more definitive analysis of the role of CD14-mediated events since the only difference between hCD14-transfected cells and cells transfected with empty vectors is the expression of human CD14. FIG. 14 shows results of an experiment wherein 70Z/3-hCD14 cells were incubated with either LPS, B. subtilis cell walls or LAM. Like LPS, cell walls and LAM induced a significant increase in the upregulation of IgM when hCD14 was expressed on the surface of the cells, indicating a definite involvement of CD14 in the response of these different agonists. As has been previously described for LPS (Lee, et al., supra, 1993), cell activation by Gram-positive cell wall and LAM was independent of whether CD14 was expressed as a GPI-anchored or a transmembrane protein.

Figure 15A:
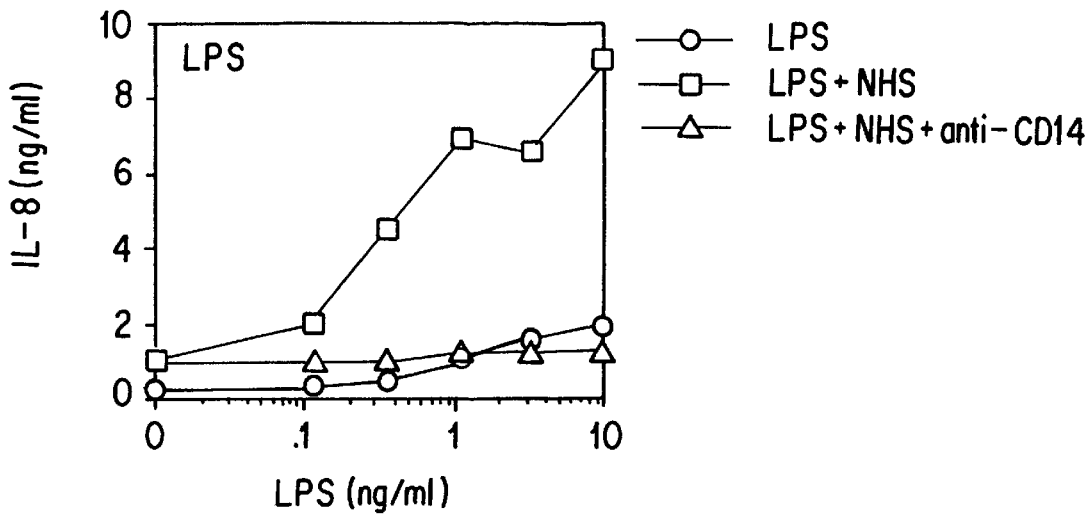
FIG. 15A displays graphs of IL-8 secretion by SW620 cells in response to LPS. Agonist only=open circles; agonist plus 2% normal human serum=NHS, open squares; agonist plus 2% NHS with 0.25 mg/ml goat anti-human CD14 IgG antibody=open triangles.
Figure 15B:
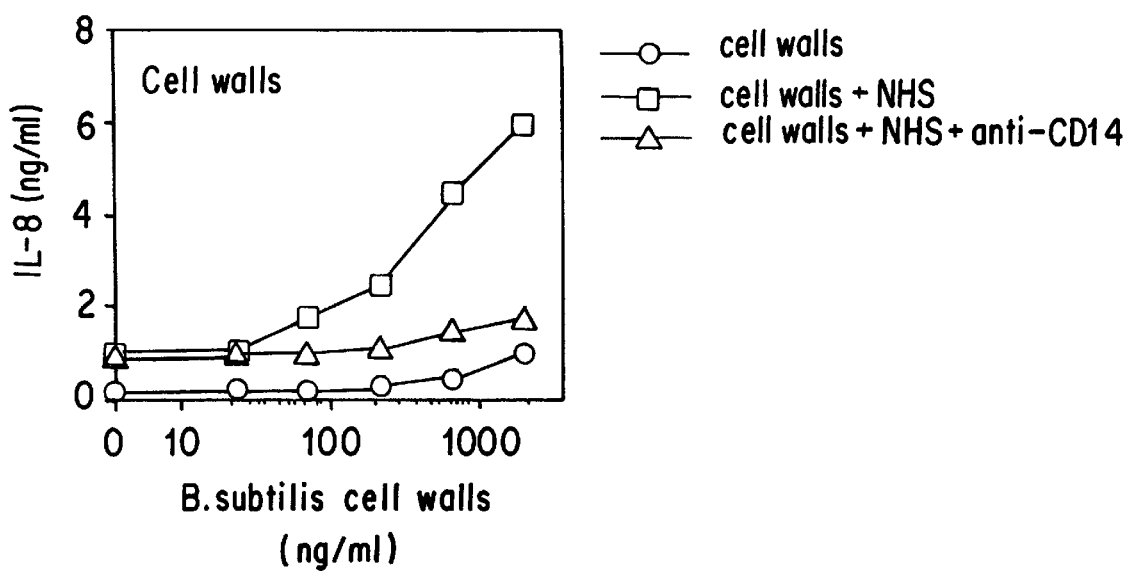
FIG. 15B displays graphs of IL-8 secretion by SW620 cells in response to B. subtilis cell walls. Agonist only=open circles; agonist plus 2% normal human serum=NHS, open squares; agonist plus 2% NHS with 0.25 mg/ml goat anti-human CD14 IgG antibody=open triangles.

Next studies were conducted to determine whether a cell line lacking membrane-bound CD14, but known to respond to LPS via a soluble CD14 (sCD14)-dependent pathway, could be activated by Gram-positive bacterial cell walls via a sCD14-dependent mechanism. Previous studies by Pugin, et al., supra, 1993a) have documented the importance of sCD14 in activation of cell lines such as SW620 cells derived from a colonic adenocarcinoma. SW620 cells are stimulated by B. subtilis cell walls and this response requires the presence of serum. As shown in FIG. 15, rabbit anti-murine CD14 polyclonal antibody blocked IL-8 release by these cells to the same extent as that observed in an LPS-induced activation system. In studies not shown here, it was also found that Gram-positive bacterial cell wall preparations induced human endothelial cell activation to a similar extent as that observed with LPS. These results show that soluble CD14 mediates Gram-positive cell wall-dependent activation of human non-CD14 bearing cells.

BINDING OF GRAM-POSITIVE CELL WALLS OR LIPOARABINOMANNAN TO CD14

Figure 16A:
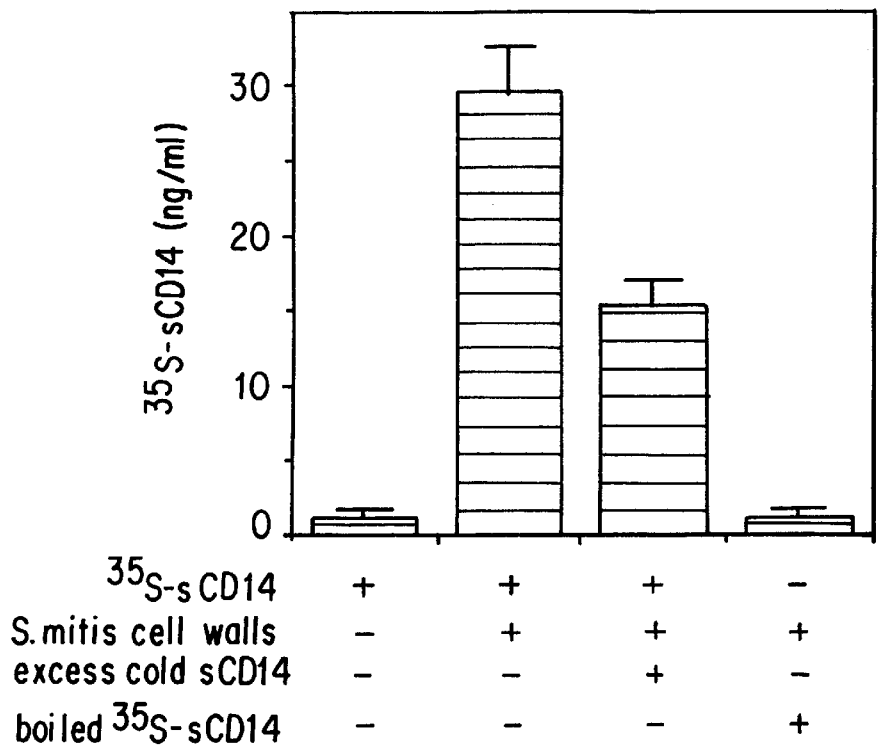
FIG. 16A is a graph showing binding of $^{35}$SsCD14 to Gram-positive toxigenic cell wall components.

Two independent experiments provide biochemical evidence for direct interactions between CD14 and bacterial cell envelope components. Binding of sCD14 to Gram-positive cell walls was obtained using $^{35}$S-sCD14. As shown in FIG. 16, $^{35}$S-sCD14 bound to cell walls, the binding was inhibited by the presence of an excess of unlabelled sCD14, and binding was abrogated when $^{35}$S-sCD14 was denatured by heating at 100° C. for 5 min as shown in FIG. 16A.

Figure 16B:
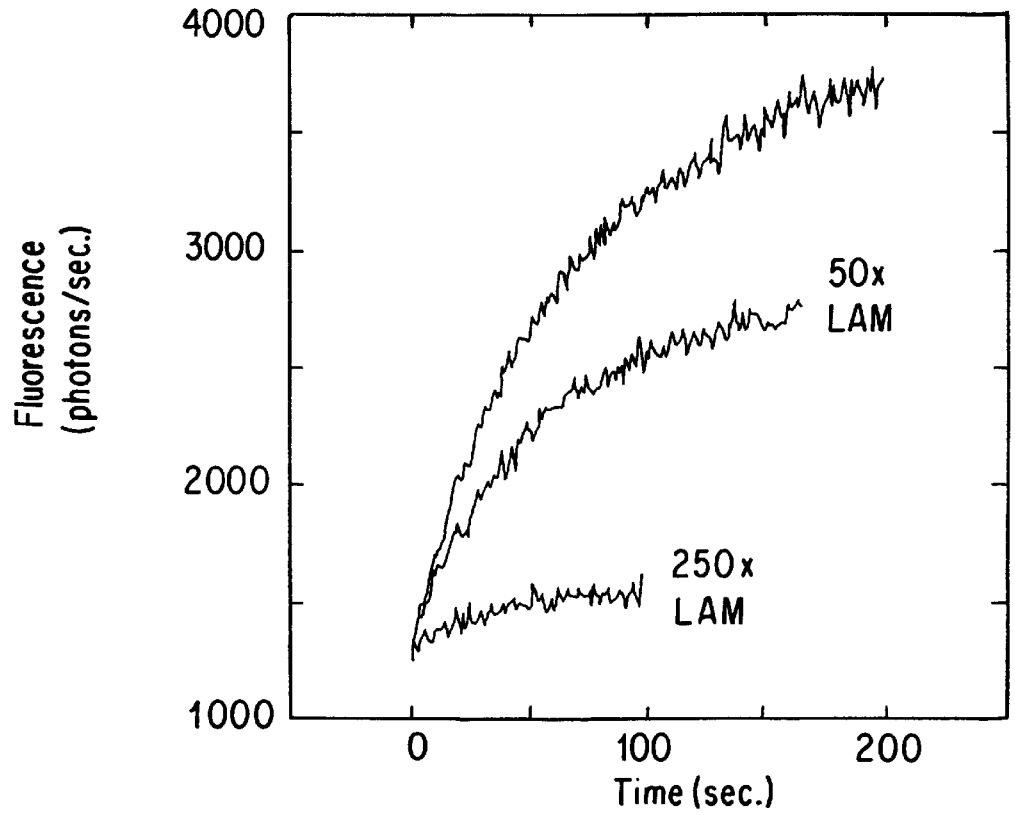
FIG. 16B is a graph showing competition by LAM for FITC-Re595-LPS binding to soluble CD14. Either no LAM (upper curve) or LAM in 50-fold or 250-fold weight/weight excess over LPS (lower curve) was added to a mixture of FITC-LPS, LBP and soluble CD14. Changes in fluorescence of FITC-Re5 95-LPS were recorded over time in a SLM 6000 fluorimeter.

A spectrofluorometric assay was developed to monitor the interactions between FITC-ReS95/LPS and sCD14. When FITC-ReS95 LPS binds to sCD14 a marked increase in fluorescence intensity is noted that occurs rapidly over a period of several minutes (FIG. 16B, upper tracing). When excess LAM was added to reaction mixtures, a marked inhibition of the increase in fluorescence intensity of FITC-ReS95-LPS was observed (FIG. 16B, middle and lower tracing). These data indicate a competition between LAM and LPS for the binding to sCD14.

Based on the studies presented herein, it is believed that the myeloid receptor CD14 serves as a recognition molecule for a wide variety of bacterial envelope molecules, such as the LPS from Gram-negative organisms, mycobacterial lipoarabinomannan and (a) component(s) of Gram-positive cell walls. Interaction of these agonists with macrophages through CD14 leads to cell activation. Although not wishing to be bound by the mechanism of molecular recognition, it is believed that CD14 is a pattern recognition receptor with multiple microbial ligand binding specificities.

The immune response to infectious microorganisms in vertebrates is a two step event with an initial nonadaptive (innate) immunity, followed by an adaptive immunity with expansion of specific clonal defenses. Myeloid cells play a central role during the nonadaptive (early) phase of defenses against microbes. Recognition of infectious particles by macrophages leads to a rapid activation of nonspecific defenses, with production of monokines (TNF, IL-1, or IL-6), various enzymes, and oxygen and nitrogen radicals. As recently proposed by Janeway, supra, 1992, it is very likely that nonclonal immune receptors detect common or highly conserved constituents of pathogenic microorganisms. Evolutionary pressure would have selected such receptors for their broad recognition properties. Interaction of different microbial surface structures through the same receptor would trigger nonspecific responses typical of the innate immunity. CD14, with its polyspecificity for microbial structures as demonstrated by the Examples herein, is a prototypic example of such receptors. Other surface proteins of mammalian cells may recognize different bacterial components. Certainly the members of the scavenger receptor family have been shown to have such properties (Krieger, et al., *J. Bio. Chem.,* 268:4569–4572, 1993). However, unlike CD14, this group of proteins does not participate in cellular activation, but seems to finction in uptake of ligands from the extracellular environment.

Microbial structures recognized by polyspecific nonadaptive receptors must be highly conserved among pathogens and critical for microbe integrity or pathogenicity. LPS fulfills these criteria for the group of Gram-negative bacteria. LPS is necessary for Gram-negative pathogenicity, is highly conserved, and is recognized by CD14. Lipoarabinomannan (LAM) is also a conserved critical pathogenic envelope structure in mycobacteria (Chatterjee, et al., *Infect. Immun.,* 60:1249–1253, 1992), and triggers cell activation through CD14. There are significant similarities in LPS and LAM structures. Both molecules are amphophilic, with hydrophobic lipid acyl chains at one end and hydrophilic polysaccharides at the other end (Tobias, et al., supra, 1992; Prinzis, et al., *J. Gen. Microbiol.,* 139:2649–2658, 1993).

In Gram-positive cell walls, the structure responsible for macrophage activation through CD14 is unknown. However, this structure seems to be highly conserved among different Gram-positive bacteria, since cell walls from all the strains tested activated macrophages in a CD14-dependent manner. Candidates for the principal ligands of Gram-positive cell walls that bind to CD14 include monomers or oligomers of muropeptides or teichoic acid fragments.

The inventors herein have discovered that some cells which do not bear CD14 respond to a wide variety of microbial structures through a soluble-CD14 dependent pathway, namely endothelial and epithelial cells. Once activated, these cells are critical for leukocyte trafficking in tissues, to secrete cytokines, oxygen and nitrogen radicals, and to modulate coagulation. These cells may, therefore, participate in the early, nonspecific events of immunity to infectious organisms in concert with macrophages. It is interesting to notice that endothelial cells and some epithelial cells are also potential antigen-presenting cells, and may participate with macrophages or dendritic cells in the initiation of the adaptive, clonal phase of immunity (Hughes, et al., *Immunol. Rev.,* 117:85–102, 1990).

In a recent study (Heumann, et al., supra) demonstrated that serum was required for activation of human monocytes by Gram-positive cell wall products (Heumann, et al., supra). These authors found that an anti-CD14 mAb (MY4) did not block activation of primary human monocytes triggered by large amounts (1–10, ug/ml) of Gram-positive cell walls. In our studies, a CD14 dependency was observed only with low concentration of agonists (300 ng/ml and below). In addition, anti-CD14 mAb MY4 may recognize a functional domain that is not critical for Gram-positive cell wall binding to CD14. These facts may explain the apparently discrepant results between these studies.

Experiments with macrophages from C3H/HeJ mice indicate that in spite of the fact that various agonists induce similar cell responses through CD14, these agonists do not seem to share the same activation pathway. C3H/HeJ macrophages are typically resistant to LPS but can be activated with other agonists, such as LAM (Chatterjee, et al., supra) or whole heatkilled Gram-positive bacteria (Freudenberg and Galanos, *Infect. Immun.*, 59:2110–2115, 1991). Importantly, we found that C3H/HeJ macrophages responded to LAM and Gram-positive cell walls in a CD14-dependent manner. It has previously been proposed that the GPI-anchored membrane form of CD14 mediates intracellular signalling via a putative transmembrane transducer (Ulevitch and Tobias, supra). The results of the experiments discussed herein indicate that either the same putative transducer has different epitopes for different agonists or that different transducing molecules exist at the surface of the cell and recognize only a specific agonist "presented" by CD14. The very specific LPS deficiency in C3H/EleJ mice could then be explained by a mutation in the LPS site of the polyspecific signal transducer or by the functional lack of the LPS specific signal transducer.

In summary, we show that CD14 in its membrane-bound form (myeloid cells) or in its soluble form (endothelial and epithelial cells) mediates cellular activation in response to a wide variety of conserved molecules from pathogenic bacterial envelopes. We propose CD14 as a prototype of a receptor/mediator for nonadaptive, nonspecific early immune response to pathogenic microorganisms. Therapeutic agents modulating CD14 functions provide great hope for treatment and/or prevention of many different deadly bacterial diseases. In the case of bacterial sepsis, blocking CD14 functions with anti-CD14 antibodies can prevent potentially deleterious overwhelming host responses to Gram-negative or Gram-positive bacteria.

EXAMPLES

The following examples are intended to illustrate, but not limit, the present invention.

Examples 1–11 illustrate studies establishing that human cells of the monocyte/macrophage lineage bind LPS-LBP complexes via a cell surface receptor that is mobile in the plane of the membrane. Example 12 illustrates that anti-CD14 antibodies can specifically inhibit the binding of LPS-LBP complexes to CD14. Examples 13–15 demonstrate that CD14 specifically binds LPS-LBP complexes and that binding induces TNF secretion from MO. Example 16 demonstrates that anti-CD14 mAbs inhibit LPS-LBP complex induced TNF secretion in human blood. Example 17 provides a summary and discussion of the results of Examples 1–16.

1. Reagents

LBP was purified from acute phase rabbit serum (Tobias, et al., supra., 1986), and appeared homogeneous on silver stained gels. Anti-rabbit LBP was raised in goats. MBP was obtained from Dr. R. A. B. Ezekowitz (Boston, Mass.). Bactericidal/permeability-increasing factor (BPI) was obtained from Dr. J. Gabay (New York, N.Y.). LPS from *Salmonella minnesota* (Re595 or wild type) was obtained from List Biological (Campbell, Calif.). Monoclonal antibodies (mAbs) IB4 against CD18 and 3G8 against FcγRIII (CD16) were described in Wright, et al. (*Proc. Natl. Acad. Sci USA*, 80:5699–5703, 1983). mAb 543 against CR1 was obtained from Dr. R. Schreiber (St. Louis, Mo.), and mAbs 22 and IV.3, against FcγRI and FcγRII, were obtained from Dr. M. Fanger (Hanover, N.H.). Pyrogen-free human serum albumin (HSA) was from Armour Pharmaceuticals, and pyrogen-free PBS and DGVB++ were from Whitaker MA Bioproducts. NHS-biotin, Sulfo-NHS-biotin, and streptavidin were from Pierce Chemical.

2. Surfaces

Tissue culture plastic surfaces were coated by incubation with 25 ug/ml protein (antibody, LBP, or HSA) or 1 (ug/ml) per microgram/milliliter LPS for 1 hour(hr) at 20° C. To form immune complexes, HSA-coated surfaces were incubated with anti-HSA antiserum (1:50) for an additional 30 minutes (min). In some cases, LPS-coated surfaces were subsequently treated with 10 ug/ml LBP for 30 min at 20° C. For assays of hydrogen peroxide production, all coated surfaces were exposed to 1 milligram per milliliter (mg/ml) HSA for 1 hr prior to the addition of phagocytes. Coated surfaces were carefully washed with pyrogen free PBS before the assays.

3. Cells

Monocyte-derived macrophages (MO) were obtained by culturing purified human monocytes in Teflon beakers for 3–10 days as described by Wright, et al. (*J. Exp. Med.*, 156:1149–1164, 1982). Monolayers of fresh monocytes were obtained by allowing peripheral blood mononuclear cells to adhere to protein-coated plastic for 45 min at 37° C. PMN were purified from fresh blood by the method of English, et al. (*J. Immunol. Methods*, 5:249, 1974). T cells, purified by rosetting with erythrocytes, were obtained from J. Ming (Rockefeller U.). Human umbilical vein endothelial cell monolayers (Lo, et al., *J. Exp. Med.*, 169:1779–1793, 1989) were obtained from Dr. S. K. Lo (Rockefeller U.).

Sheep erythrocytes (E) were coated with IgG (EIgG) or IgM (EIgM) as described by Wright, et al., supra, 1982.

C3bi was deposited on EIgM by incubating $2-10 \times 10^8$ EIgM in 1 ml of 10% C5-deficient human serum (Sigma) for 30 min at 37° C. The erythrocytes were then washed and incubated for 10 min at 0° C. in a buffer containing 2.5 mM ethylenediametetracetate (EDTA). The resulting EC3bi bore no C3b as assayed by EDTA-resistant rosetting with MO.

E were coated with LPS as described by Wright, et al. (*J. Exp. Med.*, 164:1876–1888, 1986). The amount of LPS used in the preparation was varied to yield $ELPS^{hi}$ (1–10 ug/4× $10^7$E) or $ELPS^{lo}$ (0.2–1 ug/4×$10^7$E). $ELPS^{lo}$ were coated with LBP by incubating equal volumes of $ELPS^{lo}$ ($10^8$/ml) and LBP (10 ug/ml) for 20 min at 37° C. The resulting LBP-coated ELPS (ligand-coated E) were washed and used immediately.

For some studies E were also coated with LBP by an alternative method. E were first biotinylated by incubating $5\times10^8$ E with 250 ug Sulfo-NHS-biotin for 20 min at 5 C. in 0.1 M sodium carbonate pH 9.2, and LBP was biotinylated by incubating 50 ug LBP with 5 ug Sulfo-NHS-Biotin and dialyzing against PBS. The biotinylated protein was then linked to the biotinylated E through a streptavidin bridge. $10^8$ washed, biotinylated E (EB) were incubated with 10 ug Streptavidin for 30 min at 20° C. to yield avidin coated erythrocytes (EBAV). Preliminary experiments using fluoresceinated streptavidin showed that the EBAV were uniformly and intensely fluorescent, and no agglutination could be seen. $2.5 \times 10^7$ washed EBAV were incubated with 2.5 ug of biotinylated LBP for 30 min at 20° C. to yield EBAV-LBP.

*Salmonella typhimurium* LT2 Gal E was grown in the presence or absence of galactose to yield cells with a complete or truncated LPS, respectively (Wright, et al., supra, 1986). Exponentially growing cultures were washed, labelled with fluorescein, and adjusted to $2 \times 10^8$/microliter (ul) in PBS as previously described (Wright, et al., supra, 1986).

4. Assays

Agglutination of LPS-coated erythrocytes (Example 3) was measured by shaking $10^6$ ELPS$^{hi}$ in 10 ul of diluted LBP for 30 min at 21° C. in a round bottom microtest plate. Agglutination was read from the settling pattern.

Binding of ligand-coated E (Example 3) to MO was measured as described by Wright, et al., supra, 1982. Briefly, Terasaki tissue culture plates were coated with HSA or other proteins (Example 2), and monolayers of MO were established by incubating 5 ul of cells ($0.5 \times 10^6$/ml in PBS containing 3 mM glucose, 0.5 mg/ml HSA, and 0.3 u/ml aprotinin (Sigma), for 45 min at 37° C. Ligand coated E and the indicated proteins were added to the monolayers. E were allowed to settle for 10 min at 0° C., then the plate was warmed to 37° C. for 15 min. Unattached E were removed by washing and attachment was scored by phase contrast microscopy. Binding of fluoresceinated Salmonella was assessed by a similar method employing a 15 min incubation at 37° C. as described by Wright, et al., supra, 1986. Results are reported as attachment index, the number of E or bacteria per 100 MO. Phagocytosis of ligand-coated E was measured by similar methods (Wright, et al., supra, 1982), with the exception that incubation of MO with the E was for 45 min at 37° C., and uningested E were lysed by brief exposure to hypotonic medium before scoring the wells.

5. LBP Binds To LPS Inserted Into Erythrocyte Membranes

Addition of as little as 0.5 ug/ml of LBP to ELPS$^{hi}$ caused agglutination. Since LPS partitions into the membrane of E by hydrophobic interactions with phospholipids, this observation suggests that LBP recognizes the exposed hydrophilic portion of lipid A, and that LBP has the potential to form multimers. The ELPS were not strongly agglutinated and could be disrupted by gentle pipetting.

6. LBP Enhances Binding Of ELPS And Salmonella to Macrophages

Gram-negative bacteria and LPS-coated erythrocytes bind to MO through an interaction of LPS with members of the CD18 complex of receptors on leukocytes (Wright, et al., supra., 1986). The ability of LBP to perturb that interaction was, therefore, examined. Initial studies employed E prepared with high levels of LPS. These ELPS$^{hi}$ bound avidly to MO, and the addition of LBP slightly enhanced binding. To examine the nature of this enhancement, E were prepared with low levels of LPS. Monolayers of MO were incubated with ELPS$^{lo}$ in the presence or absence of 5 micrograms (ug) per milliliter (ml) LBP. ELPS$^{lo}$ were poorly bound by MO, but the addition of LBP caused a dramatic enhancement of binding (FIG. 1). Enhanced binding was dose dependent with a maximal effect at 1 ug/ml LBP. The specificity of this effect is indicated by the observation that another acute phase reactant, mannose binding protein, did not affect binding of ELPS$^{lo}$ to MO (FIG. 1) at concentrations as high as 100 ug/ml; another LPS-binding protein, BPI, did not affect binding at concentrations as high as 10 ug/ml; and polyclonal anti-LBP antiserum (1:200) caused a 20-fold reduction in the rosetting of ELPS$^{lo}$ cause by LBP.

Figure 2:
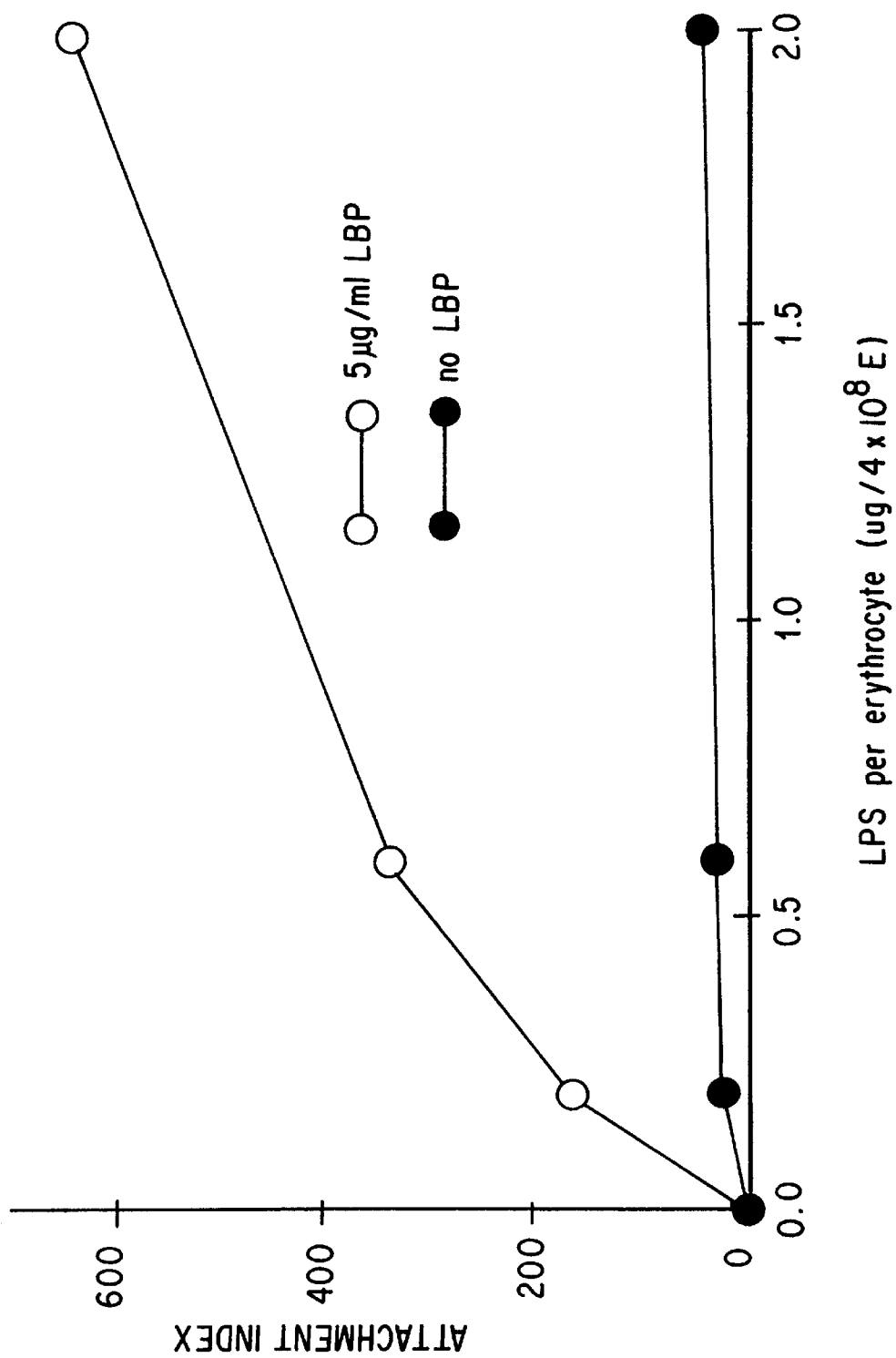
FIG. 2 illustrates LBP-dependent binding of ELPS to MO depends on the density of LPS in the E membrane. ELPS were prepared with varying doses of LPS then incubated with monolayers of MO in the presence or absence of 5 ug/ml LBP. Results are representative of 4 separate experiments.

The capacity of LBP to enhance interaction of ELPS with MO was also dependent on the amount of LPS in the erythrocyte membrane (FIG. 2). LBP could effectively mediate binding of E prepared with amounts of LPS 20–100 fold less than the amount needed to sustain a direct interaction between ELPS and MO.

Strains of Gram-negative bacteria that express a truncated LPS (rough strains) are avidly bound by MO, but smooth strains, with a complete LPS, are bound poorly (Wright, et al., supra, 1986). Because LBP binds equally well to both smooth and rough LPS (Tobias, et al., supra, 1989), the ability of LBP to opsonize smooth Salmonella was examined. As illustrated by the data shown in Table II, the addition of LBP caused a dramatic enhancement in the binding of smooth Salmonella to MO.

TABLE II

LBP Enhances Binding Of Salmonella To MO[1]

| Attachment Index | smooth *S. typhimurium* | rough *S. typhimurium* |
| --- | --- | --- |
| −LBP | 273 | 1,096 |
| +LBP | 1,661 | 2,109 |

[1]Smooth and rough form preparations of *S. typhimurium* LT2 were obtained by growing GalE mutants of this strain in the presence or absence of galactose as described by Wright, et al. (J. Exp. Med., 164:1876–1888, 1986). The binding of bacteria to monolayers of macrophages was then measured in the presence of absence of 2.5 ug/ml LBP. Addition of LBP caused a 5.9 ± 1.9 (n-4) fold enhancement in the binding of smooth bacteria to MO.

Table II illustrates that the addition of LBP also enhanced the binding of rough Salmonella, but the effect appeared less dramatic than that seen with smooth *S. typhimurium* due to the avid binding of unopsonized bacteria. Thus, LBP can enhance the interaction of live, intact bacterium with MO.

7. MO Recognize Complexes Of LBP With LPS

In Example 6, LBP was added together with the MO and the ELPS. To determine if LBP binds to MO or ELPS, the cells were separately incubated (treated) with LBP, washed, and then combined. The results of this study are shown in Table III.

TABLE III

Pretreatment Of ELPS But Not MO With LBP Enhances Their Interaction[1]

| | Condition | | |
| --- | --- | --- | --- |
| Attachment Index | Study 1 | Study 2 | Study 3 |
| no LBP | 6 | 17 | 4 |
| Pretreat ELPS$^{lo}$ | 820 | 715 | 942 |
| Pretreat MO | 5 | 21 | 16 |
| coincubate LPB, ELPS$^{lo}$ and MO | 629 | 520 | 796 |

[1]Binding of ELPS$^{lo}$ (0.2 ug/4 × $10^8$ E) to monolayers of MO was measured as described in Example 4. ELPS$^{lo}$ or MO pretreated at 37° C. with 5 ug/ml for 20 min and washed before the assay. Alternatively, 5 ug/ml LBP was added during the assay of attachment.

Pre-treatment of ELPS$^{lo}$ with LBP strongly enhanced binding to MO (Table III) with a dose response curve identical to that observed in the coincubation experiments (data not shown). This result suggests that LBP associates stably with ELPS and that the surface-bound LBP is recognized by MO. Pre-treatment of MO, on the other hand, did not affect the subsequent binding of ELPS (Table III).

Figure 3:
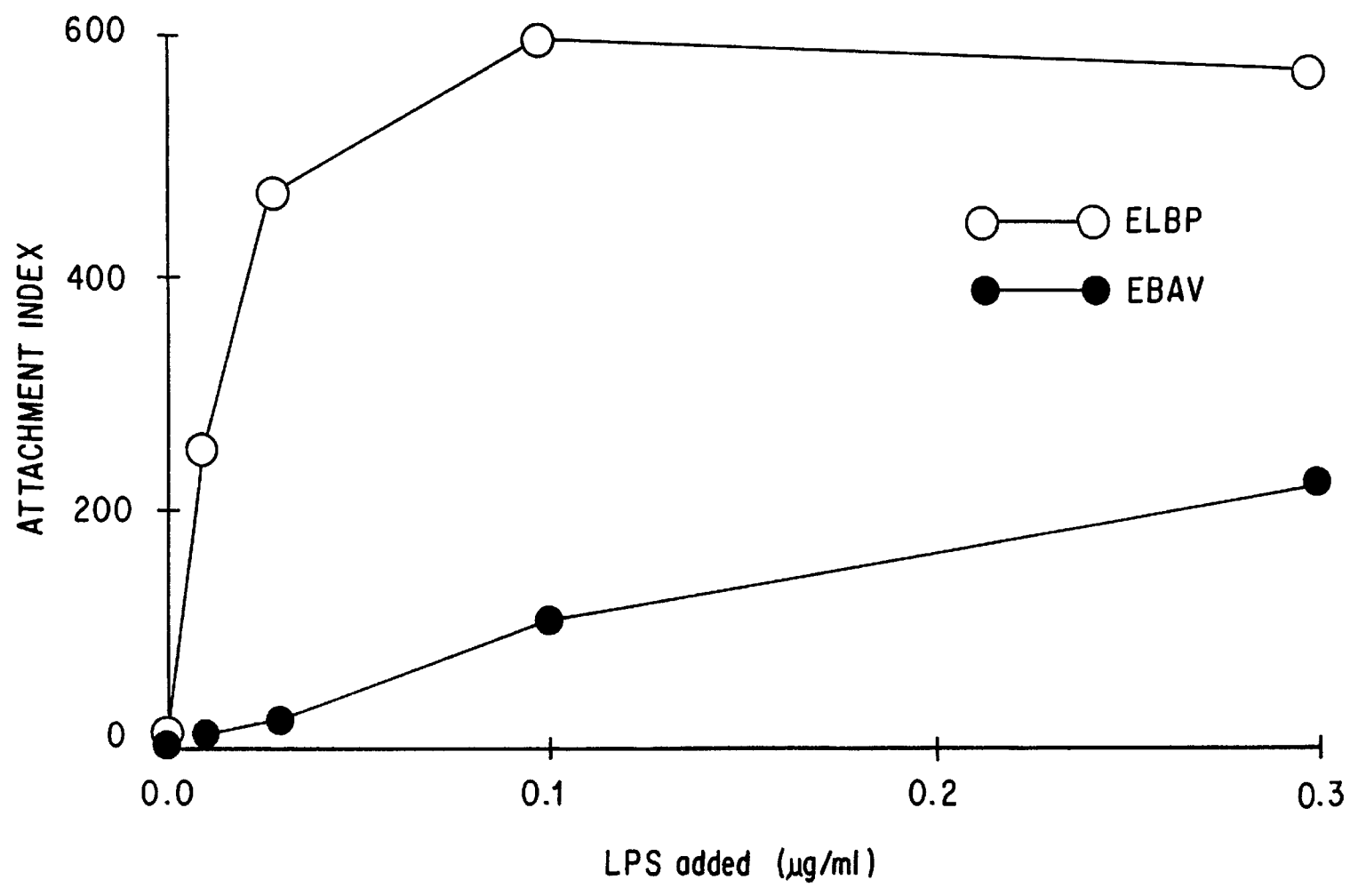

LBP on the surface of ELPS is complexed with LPS. To determine if MO bind to LBP in the absence of LPS, LBP was biotinylated and attached to streptavidin-coated erythrocytes. The resulting EBAV-LBP were not bound by MO (FIG. 3), but addition of LPS caused strong attachment of ELBP to MO. The LPS appeared to enhance adherence of EBAV-LBP by binding to LBP since the amount of LPS needed to cause attachment of ELBP was ~50-fold less than needed to cause attachment of E lacking LBP (FIG. 3). Further, the LPS-treated ELBP bound avidly to CD18-deficient MO, which do not bind ELPS. Thus, LP must be complexed with LPS in order to be recognized by MO.

8. LBP Is Recognized By A Mobile Receptor Restricted To Mononuclear Phagocytes

LBP-treated ELPS bound to virtually 100% of monocytes and MO, suggesting that binding activity is present on all members of these populations. To determine whether LBP interacts with other cell types, monolayers of PMN, T-cells, and umbilical vein endothelial cells were incubated with LBP-treated ELPS$^{lo}$. No binding was observed. Similarly, lymphocytes that occasionally contaminate MO preparations were never observed to bind LBP-coated E. Thus, the capacity to bind LBP-coated particles appears to be a property restricted to mononuclear phagocytes.

The existence of a specific receptor for LBP was demonstrated by allowing MO to spread on surfaces coated with complexes of LPS and LBP. Table IV illustrates that surface-bound LBP strongly down-modulated binding of LBP-treated ELPS but had no effect on the binding ElgG or EC3bi.

TABLE IV

Receptors For LBP Are Mobile In The Plane Of The Membrane[1]

| Surface | ELPS$^{lo}$LBP | ELPS$^{hi}$ | EC3bi | EIgG |
|---|---|---|---|---|
| HSA | 833 | 507 | 915 | 621 |
| HSA-anti-HSA | 795 | 455 | 1,051 | 45 |
| IB4 | 846 | 149 | 200 | 253 |
| LPS-LBP | 147 | 628 | 1,161 | 762 |

[1]Plastic surfaces were coated with HSA (500 ug/ml), mAb IB4 (25 ug/ml) or LPS (1 ug/ml) for 2 hr at 21 C. and washed thoroughly. Where indicated, anti-HSA (1:40 dilution of rabbit anti-HSA antiserum) or LBP (5 ug/ml) was added and incubated for 30 min at 20 C. MO were allowed to spread on the washed, coated surfaces for 45 min at 37 C., and after an additional wash, the ligand-coated erythrocytes were added. ELPS$^{hi}$ were prepared with 3 ug LPS/4 × 10$^7$E. ELPS$^{lo}$ were prepared with 0.3 ug LPS/4 × 10$^7$E then treated with 5 ug/ml LBP as described in Example 3. Data shown are representative of four separate experiments.

The above results indicate that LBP is recognized by a molecule that is mobile in the plane of the membrane, and suggest that this receptor is different from CR3 and FcR.

9. LBP Does Not Interact With CR3 Or FcR

Because LPS is known to be recognized by CR3 and other members of the CD18 complex (LFA-1 and p150,95) (Wright, et al., supra, 1986), it appeared possible that LBP enhanced binding of ELPS by facilitating the interaction of a low amount of LPS with these receptors. Several observations, however, rule out this possibility. The results illustrated in Table V indicate that LBP caused strong binding of ELPS to monocytes isolated from two patients with a congenital deficiency of CD18. The CD18-deficient cells exhibited negligible binding of ELPS$^{hi}$ or EC3bi in parallel assays.

TABLE V

LBP Mediates Binding Of ELPS$^{lo}$ To Monocytes From CD18 Deficient Patients[1]

| | Subject | | | |
|---|---|---|---|---|
| Attachment Index | ELPS$^{lo}$ | ELPS$^{lo}$ + LBP | EC3bi | ELPS$^{hi}$ |
| Control 1 | 108 | 31 | 282 | 129 |
| Control 2 | 185 | 27 | 437 | 162 |
| Patient 1 | 17 | 15 | 394 | 4 |
| Patient 2 | 5 | 14 | 529 | 16 |

[1]Monolayers of monocytes from two CD18 deficient patients (CD18 deficient leukocytes respond to LPS in vitro) and two normal adult controls were incubated with EC3bi, ELPS$^{hi}$ (3 ug/4 × 10$^8$E), ELPS$^{lo}$ (1 ug/4 × 10$^8$E), and attachment index was measured. Where indicated, 2.5 ug/ml LBP was added with the ELPS$^{lo}$.

Further evidence against the participation of CD18 molecules in recognition of LBP-treated ELPS$^{lo}$ comes from experiments in which CD18 molecules were depleted from the apical surface of MO by allowing them to spread on surfaces coated with anti-CD18 mAbs. Ma IB4 down-modulated CD18 molecules as shown by the decreased binding of EC3bi and ELPS$^{hi}$, but LBP-treated ELPS bound normally to these cells (Table IV). Finally, depletion of Ca++ and Mg++ completely blocks binding of both C3bi and LPS to the CD18 complex (Wright, et al., supra, 1982; and Wright, et al., supra, 1986), but binding of LBP-treated ELPS$^{lo}$ was equivalent in EDTA-containing buffers.

The participation of Fc receptors in the recognition LBP was also ruled out. Spreading of cells on an immune-complex coated surface strongly down-modulated Fc receptors as assayed by the binding of EIgG. However, the binding of LBP-coated ELPS$^{lo}$ was unaffected (Table IV). Similar studies showed that surface-bound mannose binding protein and surface-bound mAbs against FcRI, FcRII, FcRIII, and CR1 had no effect on the binding of LBP to MO. These data suggest that LBP is not recognized by CR1, CR3, FcR or mannose binding protein receptors.

10. Receptors For LBP Enhance Fc-Mediated Phagocytosis

Figure 4:
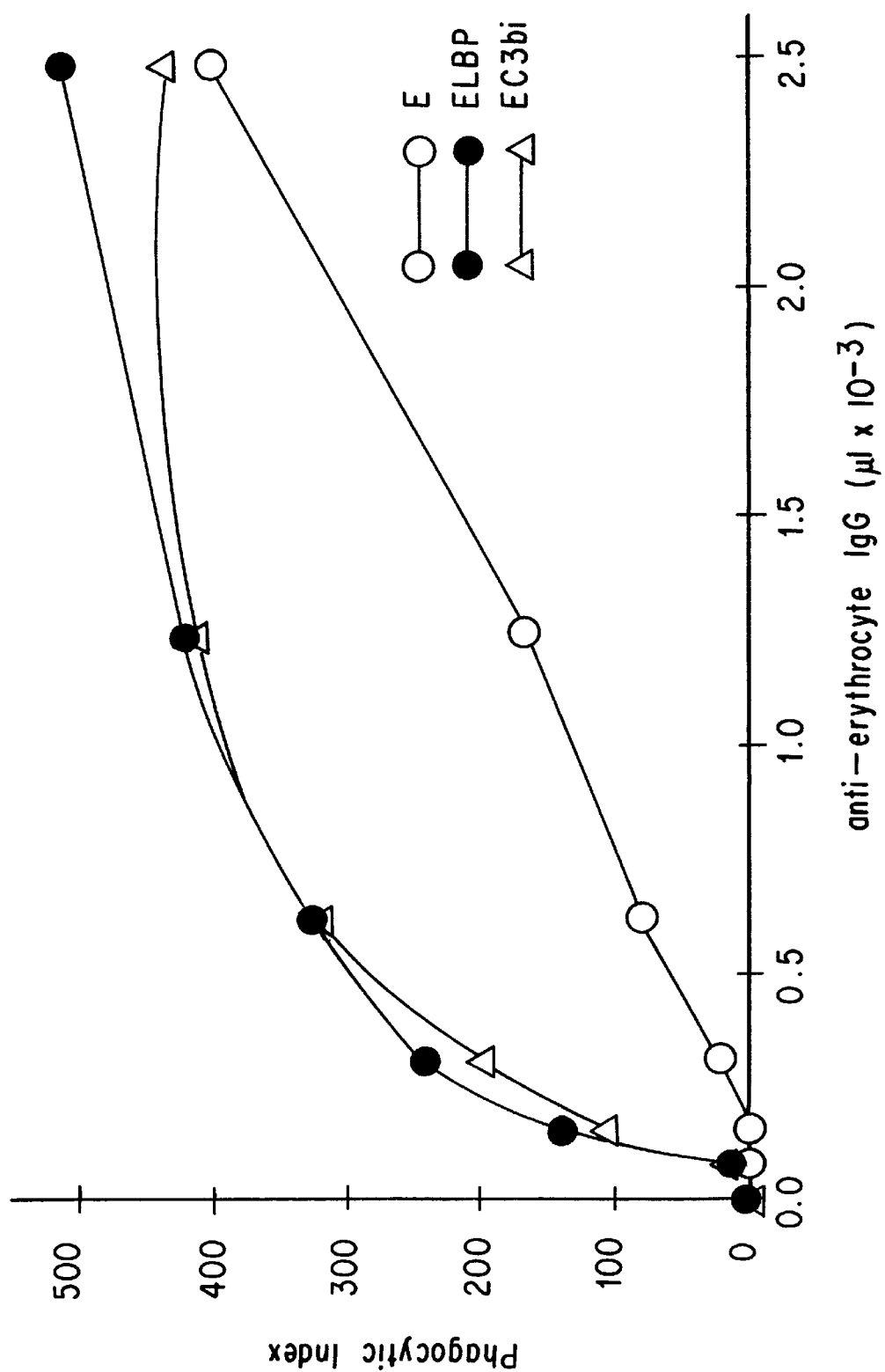
FIG. 4 illustrates that LBP enhances Fc-mediated phagocytosis. Monolayers of MO (day 5 culture) were incubated for 45 min with E, ELBP, or EC3bi in the presence of varying dilutions of anti-E-IgG. Phagocytosis of the E was determined as described in Materials and Methods. ELBP were obtained by adding 1 ug/ml LBP to ELPS$^{lo}$ (0.3 ug LPS/$3 \times 10^7$E) during incubation with MO. Attachment of these E in the absence of anti-E IgG was as follows: E, Attachment index (AI)-O; EC3bi, AI-417; ELBP, AI-404. Results are representative of six separate experiments.

Addition of anti-E IgG caused LBP-coated ELPS$^{lo}$ to be avidly phagocytosed by MO (FIG. 4). The dose of anti-E IgG needed for half-maximal phagocytosis was 5-fold less than that needed to induce phagocytosis of uncoated E (FIG. 4). LBP thus appears to act synergistically with IgG to induce a phagocytic response. In keeping with previous reports (Ehlenberger, et al., J. Exp. Med., 145:357–371, 1977), deposition of C3bi on E also enhanced phagocytosis mediated by IgG, and the extent of this enhancement was similar to that caused by LBP (FIG. 4).

Phagocytosis mediated by LBP alone was also examined. Though LBP-coated ELPS formed florid rosettes with MO, none of the bound E were phagocytosed by either resting (FIG. 4), fibronectin-, or PMA-stimulated MO. Parallel studies showed strong fibronectin- and PMA-stimulated phagocytosis of EC3bi. A possible explanation for the absence of LBP-mediated phagocytosis is the high lateral mobility of LPS on the surface of an erythrocyte. The LPS could "cap" on the pole of the E attached to the MO, leaving insufficient ligand on the circumference of the E to guide an advancing pseudopod. To prevent such capping, biotinylated LBP was linked to biotinylated E proteins as described in FIG. 4 above. Again, none of the E bound in this way were phagocytosed by either E coated resting or PMA-bistimulate MO (Phagocytic index=0). Parallel studies showed that with biotinylated F(ab)$_2$ of an anti-CD18 mAb (IB4) were readily phagocytosed (phagocytic index=482). Thus, receptors for LBP cannot by themselves initiate phagocytosis of a coated erythrocyte.

11. Receptors For LBP Do Not Initiate An Oxidative Burst

To determine whether interaction of LBP with its receptor initiates a cytotoxic response from MO, the production of hydrogen peroxide during the interaction of MO with coated surfaces was measured.

Release of hydrogen peroxide during spreading of MO on coated surfaces was measured as described by delaHarpe, et al. (*J. Immunol. Methods,* 78:323–336, 1985). Briefly, 3–4× $10^4$ MO (day 3 or 4) were added to protein-coated tissue culture wells containing horseradish peroxidase and 2.4 nmoles of scopoletin. The plate was incubated at 37° C., and at intervals the consumption of scopoletin was measured using an automated fluorescence plate reader. Results are averaged from triplicate wells and are presented as nmoles peroxide produced per well. Addition of the control stimulant, PMA (100 ng/ml), resulted in rapid evolution of peroxide that was identical in rate and extent for all coated surfaces tested.

Figure 5:
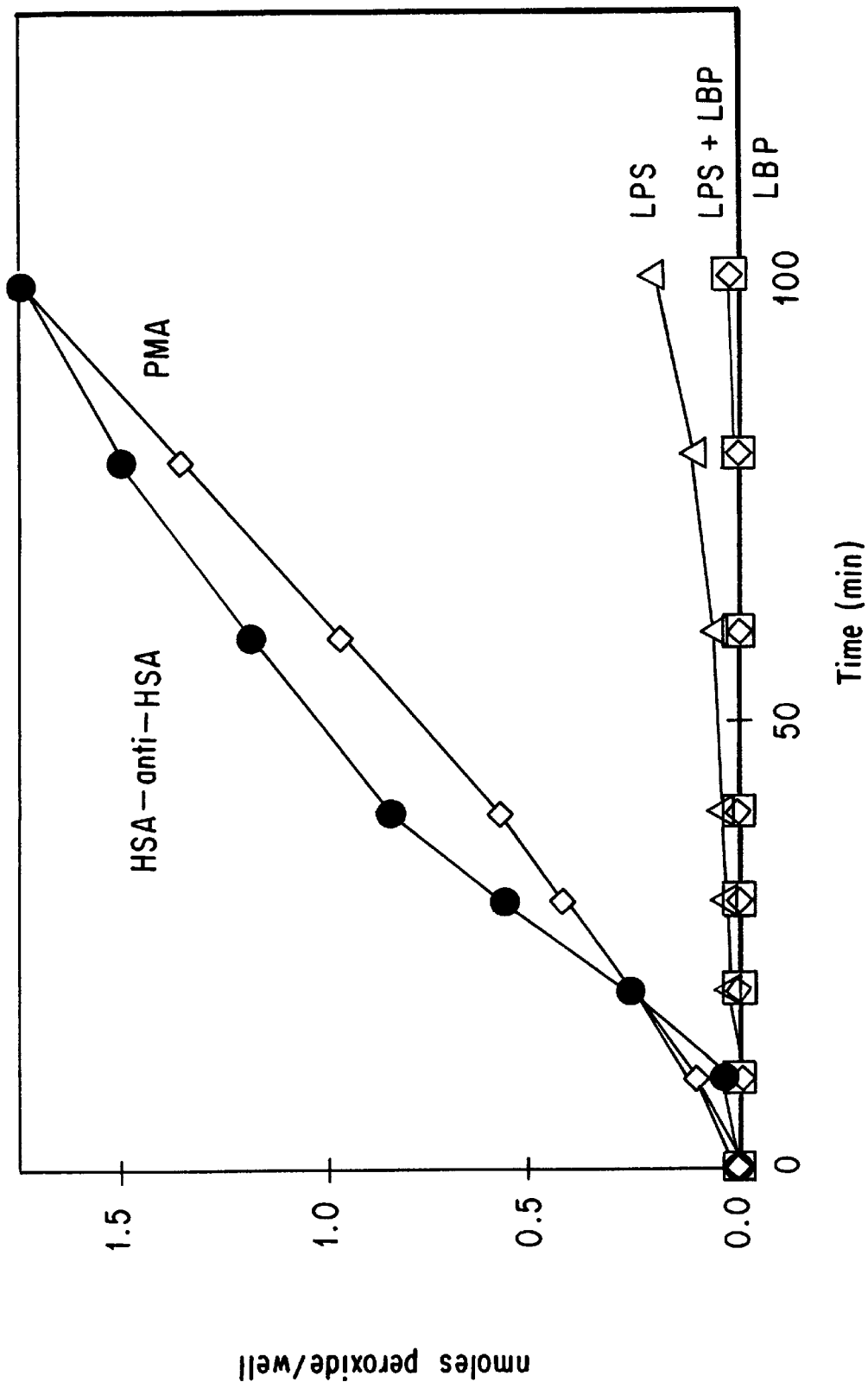
FIG. 5 illustrates that secretion of hydrogen peroxide during spreading of MO on ligand-coated surfaces. $3 \times 10^4$ MO (day 3 of culture) were added to coated microtitre wells and the evolution of hydrogen peroxide was measured at intervals. Brisk production of peroxide occurred during spreading on immune complexes (HSA-anti-HSA, closed circles) or in response to the soluble agonist, PMA (closed diamonds). Low but reproducible peroxide release was observed during interaction with LPS-coated surfaces (open triangles). However, spreading on LBP-coated surfaces (open square) caused no release, and coating of LPS-coated surfaces with LBP (open diamond) prevented the LPS-induced generation of peroxide. LBP did not impair the production or measurement of peroxide since MO in LBP-coated wells exhibited normal peroxide evolution in response to PMA.

FIG. 5 illustrates that MO binding to LPS-coated surfaces caused a small release of peroxide (12% of that stimulated by immune complexes or PMA). Surfaces coated with LBP, however, caused no release of peroxide above baseline. Further, addition of LBP to LPS-coated surfaces blocked the release caused by LPS, thus confirming that LBP effectively interacted with LPS in this experiment. Parallel experiments showed that spreading of MO on LBP or LPS+LBP-coated surfaces caused down-modulation of the binding of LBP-treated $ELPS^{lo}$, thus confirming that ligation of LBP receptors had occurred. Thus LBP receptors appear incapable of triggering an oxidative burst.

12. Inhibition Of LPS-LBP Complex Binding To MO By Anti-CD14 Antibodies

The ability of three anti-CD14 mAbs to inhibit the binding of LPS-LBP complexes to MO was examined. Monolayers of human MO were incubated for 15 minutes at O C with mAb 3C10, 60b or 26ic at concentrations of 0 ug/ml, 0.15 ug/ml, 0.5 ug/ml, 1.5 ug/ml, 5 ug/ml, and 15 ug/ml. The ability of the monolayers to bind LBP-treated $ELPS^{lo}$ (Example 3) was assayed as described in Example 4.

Figure 6:
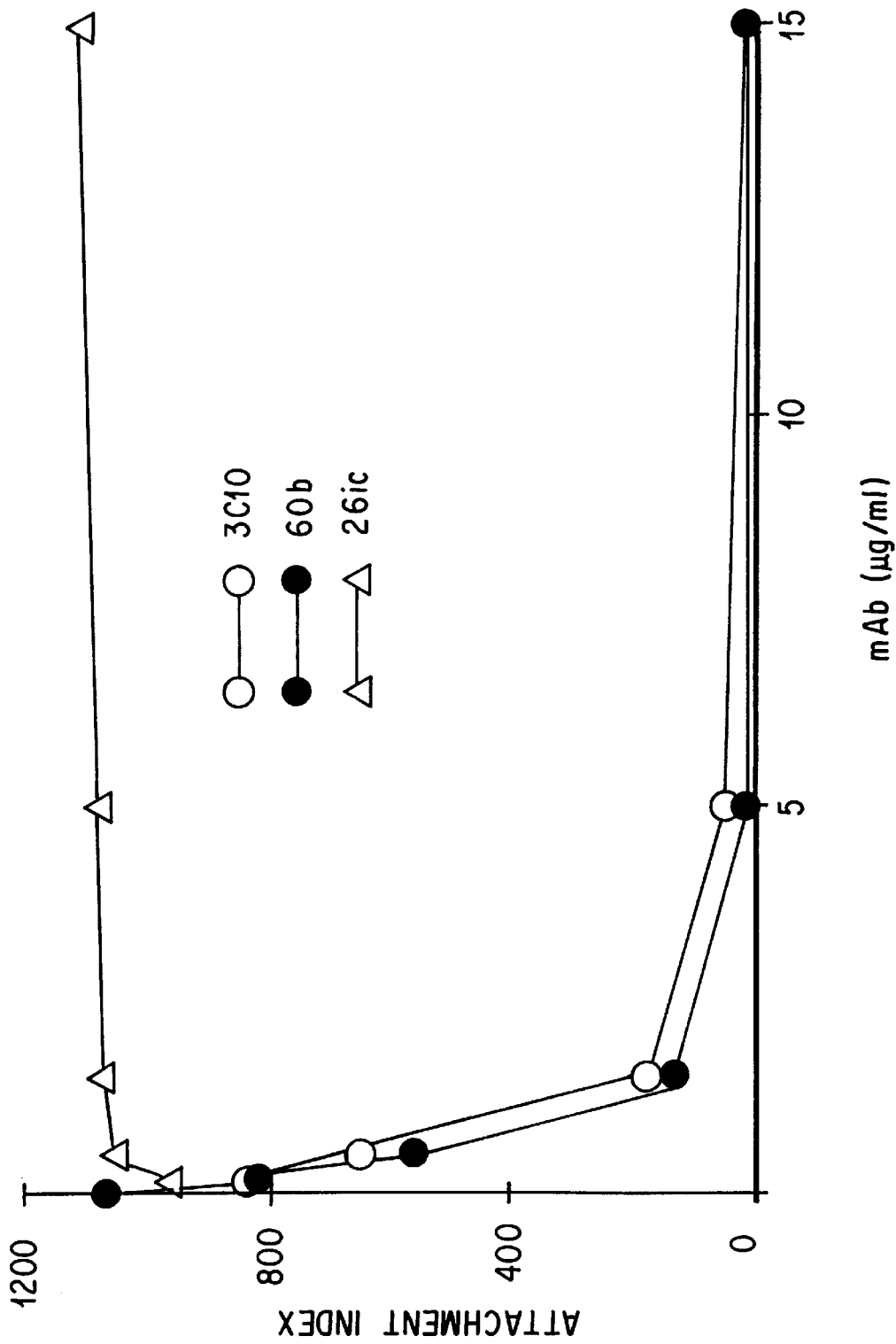
FIG. 6 illustrates the inhibition of LPS-LBP complex binding by monoclonal anti-CD14 antibodies. Monolayers of human MO were incubated for 15 min at 0° C. with the indicated concentrations of monoclonal antibodies. Erythrocytes coated sequentially with LPS and LBP were added and attachment was measured. Results are representative of three separate dose response experiments and of ten experiments performed at a fixed concentration of antibody. High concentrations of a large panel of mAbs directed against other determinants on macrophages had no effect on the binding ELBP.

The results of this study, illustrated in FIG. 6, indicate that mAbs 3C10 and 60b produced an attachment index that diminished with increasing concentration of mAb used, whereas mAb 26ic, which recognizes an epitope different from that recognized by mAbs 3C10 and 60b, failed to reduce the index below levels attained at the control mAb concentration (0 ug/ml), i.e., did not inhibit binding. Thus, mAbs 3C10 and 60b have the ability to inhibit the binding of LPS-LBP complexes to MO. The specificity of the inhibition is indicated by the observation that mAbs against CD11b, CD18, CD16 and HLA did not inhibit binding (data not shown).

Figure 7:
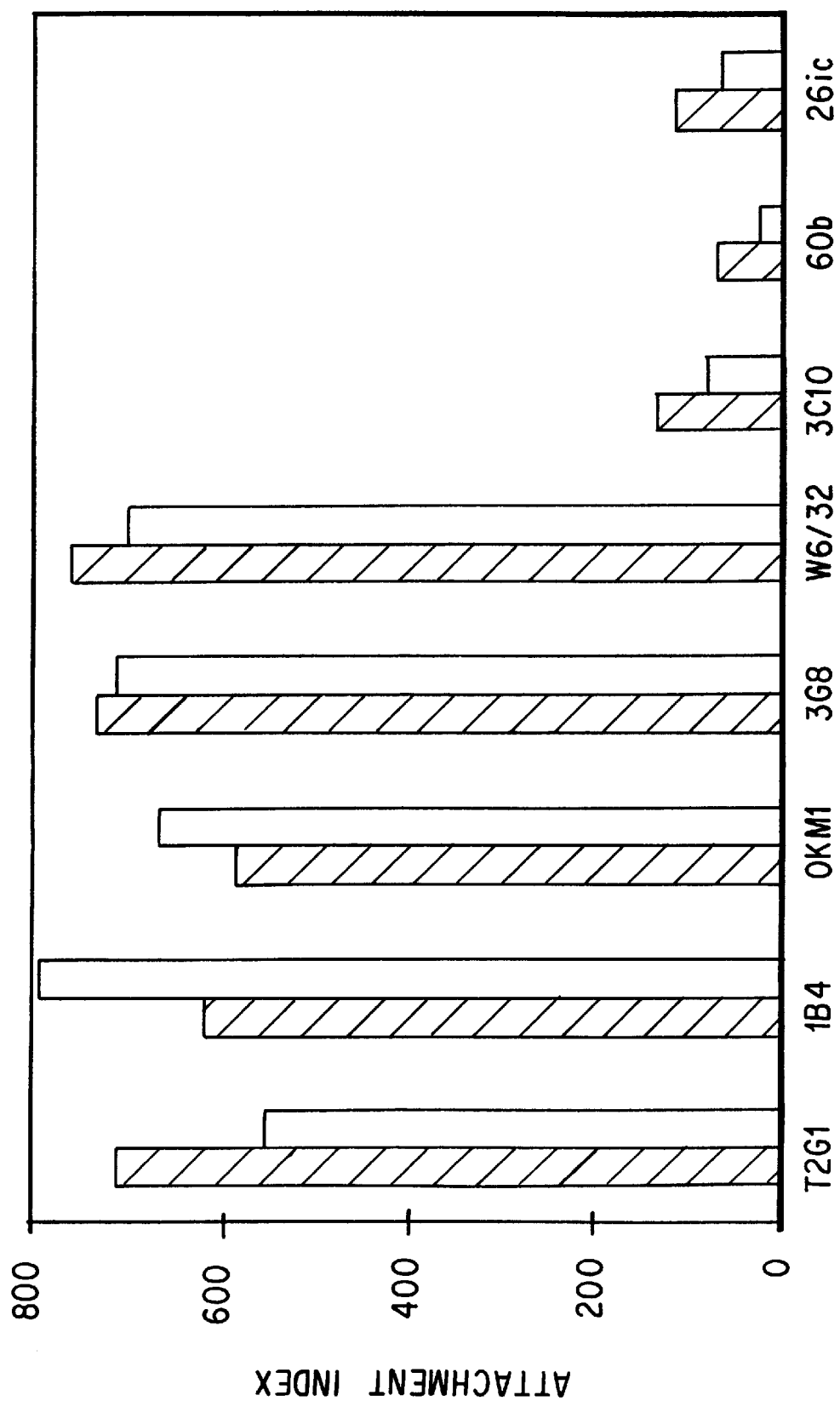
FIG. 7 illustrates that surface-bound anti-CD-14 mABs down-modulate binding of LBP-LPS complexes. Monolayers of human macrophages were established on substrates coated with 25 ug/ml of the indicated monoclonal antibodies. The cells were washed, ELPS$^{lo}$ were added, and attachment was measured.

In contrast, FIG. 7 illustrates that mAbs 26ic, 3C10 and 60b were all able to down-modulate binding of LPS-LBP complexes to MO. Monoclonal antibodies were affixed to the tissue culture plates prior to establishing the MO monolayer. This was accomplished by admixing mAb into a plate at a concentration of 25 ug protein/ml, maintaining the mAb in the plates for 60 minutes at 20 C. and then rinsing non-bound mAb from the plate prior to seeding with MO. MO attached to surfaced coated with anti-CD14 mabs, but not other mAbs, showed decreased binding of erythrocytes coated with LPS-LBP complexes. Thus, CD14 which is redistributed to the basal surface of attached macrophages, is necessary for binding of LPS-LBP complexes. This result confirms the conclusion of FIG. 6 that CD14 serves as a receptor for LPS-LBP complexes.

13. CD14 Specifically Binds LPS-LBP LBP Complexes

The ability of purified CD14 to specifically bind LPS-LBP complexes was examined. CD14 was immobilized on surfaces by coating them first with anti-CD14 mAbs then with a Triton X-100 extract of monocytes. $10^8$ monocytes were suspended in 1% Triton in PBS, incubated for 15 min at 0° C., then insoluble material was removed by centrifugation. The extract, which contains CD14, was applied to the antibody-coated surfaces. This procedure results in surfaces coated with CD14. In control wells bearing antibodies against antigens other than CD14, this procedure results in surfaces coated with proteins other than CD14. After thorough washing, erythrocytes coated with LPS-LBP complexes were added to the coated wells, and attachment of the erythrocytes ($ELPS^{lo}$) was documented by photography. CD14 adsorbed to the surface via mAb 26ic, an antibody to CD14 which does not block the binding site for LPS-LBP binding sites, strongly bound the coated erythrocytes. Surfaces coated with other antigens did not have this activity. Thus, the purified CD14 molecule has the ability to bind LPS-LBP complexes. This observation proves that CD14 serves as a receptor for LPS-LBP complexes.

14. LPS-LBP Complexes Induce TNF Secretion In MO

The ability of LPS in the presence of LBP, heat treated LBP, bovine serum albumin (BSA) or fetal calf serum (FCS) to induce TNF secretion in peritoneal exudate macrophages (PEM) was examined.

To produce rabbit PEM, NZW rabbits (2–2.5 kg) were given an intraperitoneal injection of 35 mineral oil (Drakeol 6VR, Pennreco, Butler, Pa.) containing 10 ug cell wall preparation from BCG (BCG Cell Walls, R-200, Ribi Immunochem Research, Inc. Hamilton, Mont.). Three days later, a bolus i.v. injection of 120 mg sodium pentobarbital (Western Medical Supply Inc., Arcadia, Calif.) was made, followed by aseptic lavage of the peritoneum with 500 ml ice cold RPMI-1640 GIBCO, Grand Island, N.Y.) supplemented with 2 mM L-glutamine, 1 mM Na pyruvate, 50 U/50 ug penicillin/streptomycin per ml, 10 mM Hepes, 2% fetal bovine serum and 5 U/ml heparin. The harvested cells were centrifuged (1000×G, 10 minutes, 4° C.) and resuspended in the above medium without FBS (serum-free medium). Following an additional spin and resuspension in serum-free medium, the cells were counted using a hemocytometer and plated in 150 $cm^2$ flasks at a density of 8–10× $10^7$ macrophages/flask. After 2 hrs at 37° C., 5% $CO_2$, non-adherent cells were removed from the flasks by vigorous washing and replenishment with 20 ml serum-free medium. The mineral oil induced peritoneal exudate cells, when examined using Wright's stained cytocentrifuge preparations, contained approximately 60% macrophages, 35% neutrophils and 5% lymphocytes. After plating and washing, the adherent cells were >90% macrophages. The rabbit PEM thus produced were treated with LPS isolated from Salmonella minesota Re595 (100 pg/ml) in the presence and absence of the proteins noted above for 12 hours and the cell-free supernatant assayed for TNF as described above using a modification of the L929 assay of Ruff, et al (*Lymphokines,* 2:235–242, 1981) as described in Mathison, et al. (*J. Clin. Invest.,* 81:1925, 1988).

Briefly, L929 cells (CCL 1, American Type Culture Collection, Rockville, Md.) were maintained in RPMI 1640 (GIBCO, Grand Island, N.Y.) supplemented with 10 mM Hepes and 10% fetal bovine serum (Hyclone, Rehatuin F.S., Reheis Chemical Co., Phoenix, Ariz.). Confluent cultures (3–4×$10^7$ cells/75 cm flask) were rinsed briefly with 0.5% trypsin (TRL3, Worthington Biochemical Corporation, Freehold, N.J.) in physiologic salt solution containing 5 mM EDTA and 10 mM Hepes, pH 7.4, resuspended in fresh medium containing actinomycin D (1 ug/ml) and added to 96-well plates (5–7×10⁴ cells/well). After 2 hrs in culture, serially diluted samples were added to the wells and the plates were incubated overnight (5% $CO_2$, 37° C.). Following microscopic evaluation, the medium was decanted, and the wells were filled with a solution of 0.2% crystal violet, 10% formalin and 0.01 M phosphate, pH 7–7.5 for 5 m, washed thoroughly with water and dried. The degree of lysis was quantitated spectrophotometrically (550 nm) using a Bio-Tek Model EL310 plate reader (Bio-Tek Instruments, Inc., Burlington, Vt.) interfaced with an IBM-PC computer. Assay results were expressed as U/ml, with one unit (U) defined as the amount of TNF resulting in lysis of 50% of the cells.

Routinely, 8–12 plates were set up per assay. Each plate included two laboratory standards, conditioned medium from Re595 LPS-treated RAW 264.7 cells (6×10³ U/ml) and conditioned medium from Re595 LPS-treated rabbit PEN (1.3×10³ U/ml). These standards, in turn, were calibrated against human recombinant TNF (Cetus Corporation, Emeryville, Calif., 2×10⁷ U/mg) and assay results were normalized accordingly. Samples were assayed in quadruplicate, and a coefficient of variation (SD/mean) of 0.12±0.08 (SD) was observed. Using this assay, as little as 10 pg/ml of rabbit macrophage-derived TNF (specific activity 1×10⁸ U/mg) could be detected. However, because serum concentrations greater than 10% caused nonspecific rounding and loss of adherence of the L929 cells, the lower limit of detection of rabbit TNF in serum was 20 U/ml (corresponding to 0.2 ng TNF/ml).

Figure 8:
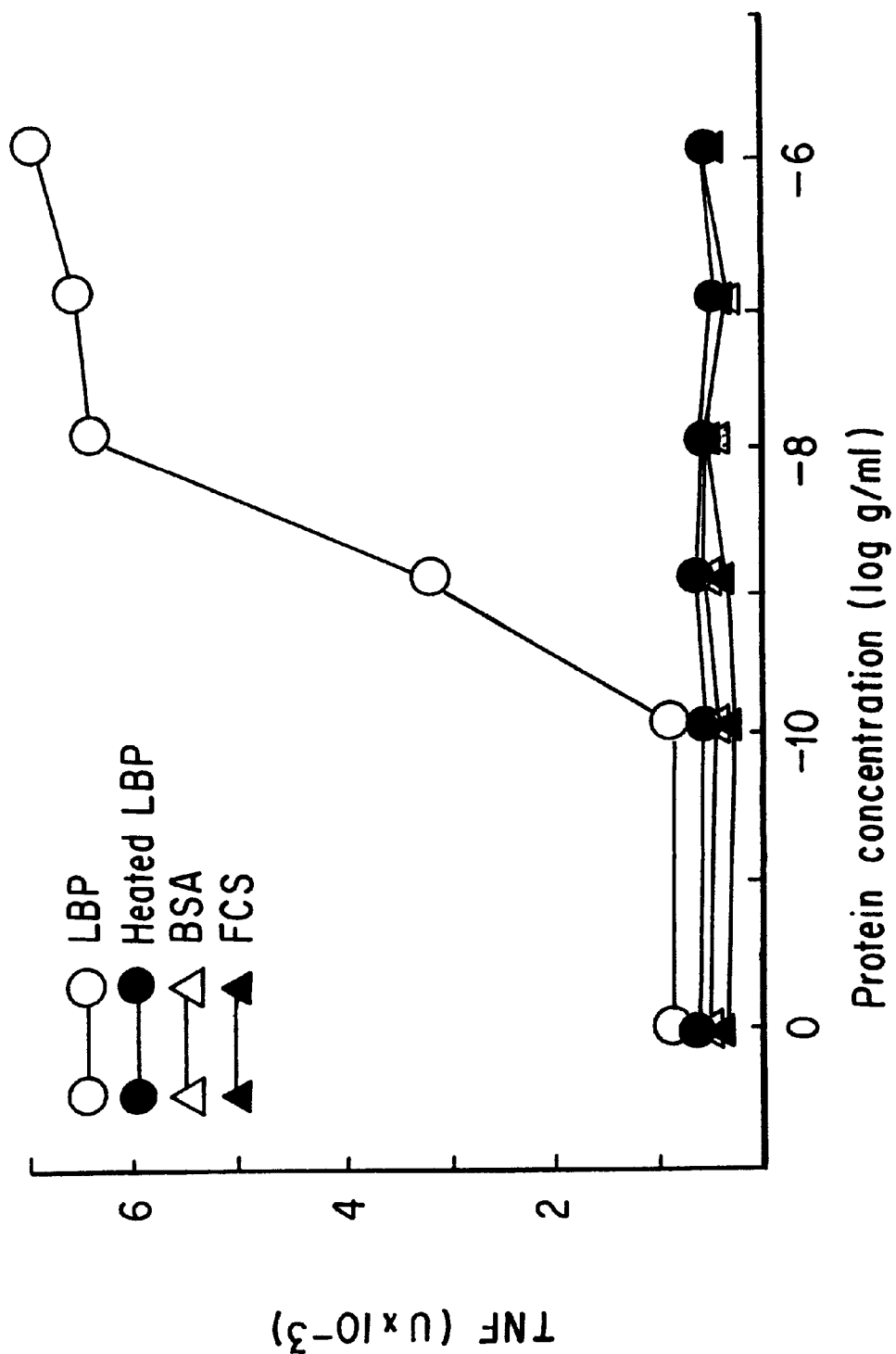
FIG. 8 illustrates that native LBP is required for LPS to induce TNF production. Rabbit peritoneal exudate macrophages (PEM) were challenged with LPS in the presence of the indicated concentrations of native LBP (LBP), heated (dentured) LBP, bovine serum albumin (BSA) or fetal calf serum (FCS). The amount of TNF produced by the challenged PEM was then determined.

The results of this study, shown in FIG. 8, demonstrate that TNF is only produced if both LPS and active LBP are present. Re595 LPS is from a rough strain of Salmonella; identical results are obtained if LPS isolated from smooth strain organisms is used such as LPS from *E. coli* 0111:B4 indicating the generality of the effects observed here.

15. The Binding Of LPS TO LBP Protects LBP from Trypsin Cleavage

Figure 9:
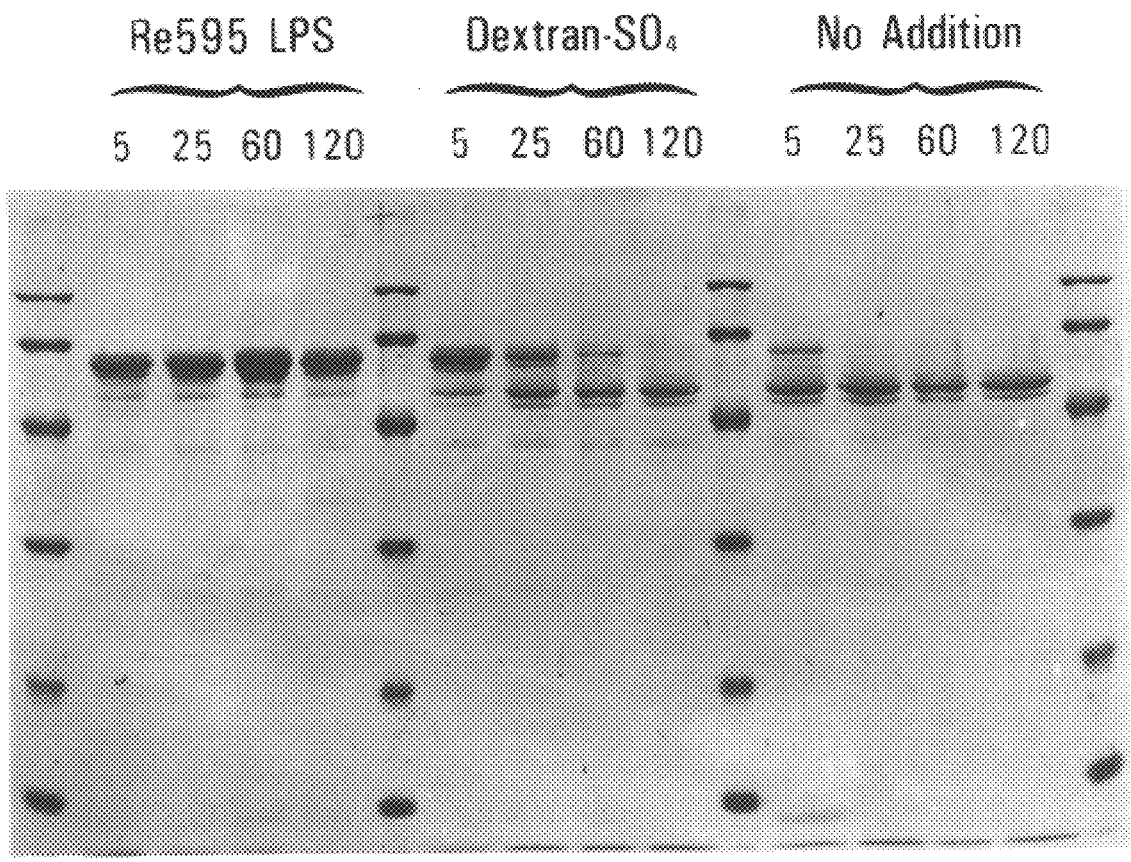
FIG. 9 illustrates the susceptibility of LBP to tryptic digestion in the presence or absence of a ligand to which it binds, i.e., Re595 LPS. Molecular weight markers (Pharmacia, Piscataway, N.J.; catalog No. 17-0446-01; phosphorylase B at 94 kilodaltons (kD), bovine serum albumin at 67 kD, ovalbumin at 43 kDa, carbonic anhydrase at 30 kD, soybean trypsin inhibitor at 20.1 kD and alpha lactalbumin at 14.4 kD.) appear in lanes adjacent to those containing LBP. The results suggest that LBP binding to LPS results in a conformational change in LBP that may account for its ability to bind CD14 only when present as part of an LPS-LBP complex.

Samples containing LBP at a final concentration of 0.3 mg/ml in a buffer containing 50 mM HEPES, 10 mM EDTA pH 7.4 were prepared. To one ample was admixed LPS to a final concentration of 0.125 mg/ml. To the second sample was admixed dextran sulfate to a final concentration of 0.125 mg/ml. Subsequently, trypsin was admixed to all three samples to a final concentration of 2 ug/ml. Aliquots were removed from the trypsin-treated samples at time intervals of 5, 25, 60 and 120 minutes while being maintained at 37 C. The aliquots were then analyzed by sodium dodecyl sulfate polyacrylamide gel electrophoresis (SDS-PAGE) using 12% gels. The results of this study, shown in FIG. 9, indicate that the binding of LPS by LBP protects LBP from enzymatic degradation. LPS may protect LBP by either inducing a conformational change in LBP that prevents cleavage or sterically hindering access to the cleavage site.

16. Anti-CD14 Monoclonal Antibodies Inhibit LPS-LBP Complex Induced TNF Production In Whole Human Blood The ability of anti-CD14 mAbs to inhibit TNF secretion by MO in human blood was examined using the TNF-induced cytotoxic activity assay described by Espevik, et al. (*J. Immunol Meth.*, 95:99–105, 1986). Briefly, whole human blood anticoagulated with heparin was prepared and incubated with mAb 3C10, 60b or IB4 at a final concentration of 1 ug/ml at 37° C. for 30 minutes. Subsequently, the cells were incubated with Re595 LPS at a final concentration of 0, 0.01, 0.1, or 1.0 ng/ml at 37° C. for 12 hours in a humidified, 10% $CO_2$ incubator. Plasma was then collected from each sample and examined for the presence of TNF.

For these studies it was not necessary to add additional LBP since constitutive levels of LBP in blood of healthy subjects is estimated to be 100–250 ng/ml (Tobias, et al., supra, 1986; and Tobias, et al., *Infect. Immun.*, 50:73–76, 1985). Based on estimates of the affinity of LPS for LBP Tobias, et al., supra, 1989, the constitutive levels of LBP are more than sufficient to bind all of the added LPS.

WEHI clone 13 cells were obtained from T. Ezpevik at University of Trondheim, Norway and cultured in RPMI 1640 culture media (Gibco) containing 10% FCS, 0.1 mM glutamine and 30 ug/ml gentamicin. The cells were seeded in microtiter plates at a concentration of 2×10⁴ cells per well in 100 microliters (ul) of RPMI 1640 culture medium. Samples of 5 to 50 microliters (ul) of MO culture supernatant was then admixed to the WEHI clone 13 cell growth media and incubated for 20 hr at 37° C. Subsequently, 10 microliters of MTT tetrazolium (M-2128 Sigma Chemical Company, St. Louis, Mo.) at a concentration of 5 mg/ml in PBS was added to each microtiter plate well and the wells were further incubated for 4 hr at 37° C. After aspirating 100 microliters of the supernatant from the wells, 100 microliters isopropanol with 0.04 N HCL was added to each well. After dissolving the dark blue formazan crystals, the plates were read on a microtiter plate reader, using a test wavelength of 570 nm and a reference wavelength of 630 nm.

Percentage of dead target cells was determined as follows:

$$= 100 - \frac{\text{optical density in wells with } CF/TNF}{\text{optical density in control wells}} \times 100$$

The percentage of dead cells obtained in the experimental cultures was then compared to the percentage obtained from various known dilutions of TNF to determine the corresponding TNF concentration of each experimental culture. The results of this study are shown in Table VI.

TABLE VI

Effect of Monoclonal Antibodies on LPS-Induced TNF Production in Whole Human Blood

| [Re595 LPS], ng/ml | Antibody[1] | [TNF], U/ml[2] |
|---|---|---|
| — | — | <0.5 |
| 0.01 | — | <0.5 |
| 0.1 | — | 4.8 |
| 1.0 | — | 39 |
| — | 3C10 | <0.5 |
| 0.01 | 3C10 | <0.5 |
| 0.1 | 3C10 | <0.5 |
| 1.0 | 3C10 | 3 |
| — | 60b | <0.5 |
| 0.01 | 60b | <0.5 |
| 0.1 | 60b | 2 |
| 1.0 | 60b | 12 |
| — | IB4[3] | <0.5 |
| 0.01 | IB4 | 2 |
| 0.1 | IB4 | 13 |
| 1.0 | IB4 | 40 |

[1]All monoclonal antibodies added at a final concentration of 1 ug/ml.
[2]TNF assays performed with the WEHI clone 13 assay using recombinant TNF having a specific activity of 2 × 10⁷ units (u) per mg as a standard.
[3]An Anti-CD18 mAB.

From Table VI it can be seen that LPS induced TNF production in whole human blood increases with increasing concentration of LPS. In addition, it can be seen that LPS-LBP complex induced TNF production was significantly inhibited by anti-CD14 monoclonal antibodies 3C10 and 60b, while the anti-CD18 IB4 monoclonal antibody produced no significant inhibition of TNF production. Similar experiments were performed with LPS isolated from the smooth form bacteria *E. coli* 0111:B4 indicating the generality of the effect on LPS preparations with varying carbohydrates content but containing conserved lipid A structures.

The TNF specificity of the cytotoxic activity found in the whole blood was established using a polyclonal goat anti-human TNF IgG antibody as described by Mathison et al. (*J. Clin. Invest.*, 81:1925, 1988). This antibody completely neutralized all of the cytotoxic activity found in the samples of LPS-treated whole blood.

17. Discussion of the Results of Examples 1–16

The foregoing demonstrates that LBP functions as an opsonin because it binds bacteria and facilitates their binding and phagocytosis by macrophages. It is believed that while LBP binds LPS through a domain which is homologous with the LPS-binding domain of BPI, the attachment of LBP to cells is mediated by a domain unique to LBP.

LBP on the surface of LPS-coated particles is recognized by a specific receptor, CD14, which on MO is mobile in the plane of the membrane. LBP-coated particles bind to CD14-expressing cells, such as MO, but not other blood cells. The binding activity on the apical surface of MO is depleted by spreading of cells on substrates coated with LBP-LPS complexes. The receptor for LBP, CD14, is distinct from other opsonic receptors since surface-bound antibodies to CR1, CR3, and FcR did not reduce the binding of LBP-coated particles.

As an opsonin LBP promotes clearance of sepsis-inducing infectious agents, such as Gram-negative bacteria. However, during sepsis bacteriolysis may occur, either through the action of endogenous lytic mechanisms including complement and degradative enzymes or following antibiotic treatments. Lysis leads to the systemic release of LPS causing increases in blood levels of LPS. Since these levels are estimated to be between 1–1000 pg LPS/ml there is sufficient LBP present to form high-affinity LPS-LBP complexes (Sturk, et al., in *Detection of Bacterial Endotoxins with the Limulus Amebocyte Lystate Test.*, eds. Watson, S. W. Allan R. Liss, New York 1987:371–385; van Deventer, S. J. H., et al., *Lancet*, 1:605–608, 1988). LPS-LBP complexes bind to CD14 on cells of the macrophage/monocyte lineage and initiate rapid synthesis and release of the monokine, TNF and thereby contribute significantly to the development of the full-blown sepsis syndrome.

The classical opsonin, IgG, facilitates the binding of IgG-coated particles, their phagocytic engulfment, and the release of toxic compounds such as hydrogen peroxide. The other classical opsonin, C3, facilitates principally the binding of C3-coated particles. Phagocytosis by unstimulated MO is observed only if the C3-coated particles also bear IgG (Ehlenberger, et al., *J. Exp. Med.*, 145:357–371, 1977), and the evolution of hydrogen peroxide is not initiated (Wright, et al., *J. Exp. Med.*, 158:2016–2023, 1983).

The opsonic activity LBP most closely resembles that of C3. LBP-coated particles are avidly bound by MO, but binding does not initiate phagocytosis or release of hydrogen peroxide (FIG. 5). LBP also acts like C3 in that it enhances phagocytosis of particles coated with low amounts of IgG (FIG. 4). The opsonic effect of LBP differs from that of C3 in only one respect. While complement proteins may initiate phagocytosis if MO are treated with an ancillary stimulus such as PMA (Wright, et al., supra, 1982) or fibronectin (Wright, et al., supra, 1983), LBP does not mediate phagocytosis even in such optimally stimulated cells.

By acting as an opsonin, LBP limits the spread of gram negative bacteria in an animal. The appearance of LBP during the acute phase makes it well suited to combating infection, and it is, therefore, believed that LBP represents a defense mechanism against infectious agents such as gram negative bacteria.

18. Cells

Murine macrophage RAW cell line 264.7 (RAW 264.7) (ATCC # TIB71), murine macrophage cell line J774.1 (J774.1)(ATCC# TIB67), L929, SW620 (ATCC# CCL227) and THP-1 (ATCC# TIB202) cell lines were obtained from ATCC, and LR9 cells isolated from mutagenized murine macrophage cell line J774.1 cells were derived as described by Hara-Kuge, et al. *J. Biol. Chem.*, 265:6606–6610, 1990, which is incorporated herein by reference. GG2EE cells, macrophages derived from C3H/HeJ mice cells, were provided by L. Varesio (National Cancer Institute, Frederick, Md.) and prepared as described by Blasi, et al. (*Eur. J. Immunol.*, 17:1491–1498, 1987), which is incorporated herein by reference. All cell lines were cultured in endotoxin-free RPMI 1640 (complete RPMI) (GIBCO) supplemented with 10% fetal calf serum (FCS) (HyClone, Logan, Utah), 2 mM L-glutamine (GIBCO, Grand Island, N.Y.), 50 yg/ml streptomycin (GIBCO) and 50 U/ml penicillin (GIBCO). SW620 cells were maintained in the identical medium except DMEM was substituted for RPMI (complete-DMEM). THP-1 cells were induced to express CD14 by treatment with 0.1 $\mu$M 1,25 dihydroxy-vitamin D3 (Biomol Research Lab, Plymouth Meeting, Pa.) as described by Tobias, et al,. supra, 1993. Murine pre-B 70Z/3 cells expressing glycosylphosphatidylinositol (GPI)-anchored (70Z/3-hCD14) or an integral membrane human CD14 (70Z/3-hCD14CI) or transfected with empty vector (70Z/3-RSV) were produced and maintained as described by Lee, et al. (*Proc. Natl. Acad. Sci. USA*, 90:9930–9934, 1993), which is incorporated herein by reference. Thioglycolate elicited murine peritoneal elicited macrophages (PEM) were obtained as described by Han, et al. (*J. Biol. Chem.*, 268:25009–25014, 1993), which is incorporated herein by reference. Isolation and maintenance of human umbilical vein endothelial cells (HUVEC) was as described by Pugin, et al., supra, 1993a; and Pugin, et al., supra, 1993b, which is incorporated herein by reference.

Heparinized (10 U/ml) whole mouse blood was obtained from Balb/c mice by cardiac puncture.

19. Reagents

Cell wall preparations from *Bacillus subtilis, Staphylococcus aureus*, group A and group B Streptococci, *Streptococcus pneumoniae*, and *Streptococcus mitis* were obtained and purified as described elsewhere (Gracia, et al., et al. *J. Biol. Chem.*, 262:15400–15405, 1987; DeJonge, et al., *J. Biol. Chem.*, 267:11248–11254, 1992; Heumann, et al., supra). Soluble peptidoglycan from *S. aureus* was obtained from R. Dziarski (Indiana University, Gary, Ind.). Lipoarabinomannan (LAM) from *Mycobacterium tuberculosis* strain H37Ra was obtained from P. Brennan (Colorado State University, Ft. Collins, Colo.). Murine $\gamma$-interferon ($\gamma$-IFN) was obtained from Robert Schreiber Ph.D. (Washington University, St. Louis, Mo.) and *E. coli* 0111:B4 LPS from List (Campbell, Calif.). Fluoresceinated ReS95 (FITC-LPS) was produced as described by Skelly, et al. (*Infect. Immun.*, 23:287–283, 1979). AntiCD14 63D3 mAb (ATCC, Rockville, Md.) was purified from ascites. Anti-CD14 28C5 mAb was obtained from D. Letureq and A. Moriarty (R.W. Johnson Pharmaceutical Research Institute, San Diego, Calif.). Anti-hIL-8 antiserum was obtained from S. L. Kunkel (University of Michigan Medical School, Ann Arbor, Mich.).

LPS contamination of LAM, Gram-positive cell wall preparations, or soluble peptidoglycan is always a concern. The freedom of agonist preparations from detectable LPS contamination was assured using the chromogenic limulus assay (BioWhittaker, Walkersville, Md.). In no case did inclusion of 50 ug/ml of polymyxin B (CalBiochem, San Diego, Calif.) block stimulation by any of the agonist substances tested except LPS itself. In addition, it was determined that LAM and Gram-positive cell walls could activate LPS-resistant C3H/HeJ macrophages whereas these cells failed to respond to as much as 100 ng/ml of E. coli 0111:B4 LPS.

20. Expression of Murine CD14 and TNF

Murine CD14 cDNA was obtained from murine macrophage RAW cell line 264.7 (RAW cell) cDNA by PCR using primers as described by Lee, et al. (*J. Exp. Med.*, 175:1697–1705, 1992) and subcloned into pDSpv3 prokaryotic expression vector, which was used to transform *E. coli* DH5α™. Bacteria from a 0.5 L overnight culture were pelleted, washed, lysed using a lysozyme-based buffer, sonicated, and solubilized in 7 M guanidine-HCl. The solubilized protein was purified by reverse-phase HPLC using a C-4 column (Pierce Chemicals, Rockford, Ill.) and an acetonitrile/trifluoroacetic acid gradient. Fractions were screened for a 41 kDa band on SDS-PAGE gel (expected molecular weight of nonglycosylated murine CD14). Protein microsequencing of the purified material revealed the expected $NH_2$-terminus sequence of murine CD14 as provided by Matsuura, et al. (*Nucleic Acids Res.*, 17:2132, 1989).

Recombinant murine TNF-α (mTNFα) was obtained using the same expression and solubilizing procedures described above except the plasmid contained a cDNA encoding murine TNFα as described by Kravchenko, et al., submitted (1994). Purification was achieved using DE-52 and hydroxyapatite ion-exchange chromatography. Microsequencing of the first 20 amino acids of the N-terminus of the purified material was identical to the published N-terminus sequence of murine TNFα. The activity of purified murine TNFα bioactivity was measured by the WEHI clone 13 mouse fibroblast bioassay as described by Espevik and Nissen-Meyer, (*J. Immunol. Methods*, 95:99–105, 1986) and found to be $7 \times 10^7$ units/mg protein.

21. Production and Characterization of Anti-murine CD14 Antibody

Eight subcutaneous immunizations of 100 μg recombinant murine CD14 were given to New Zealand White rabbits over a 24 week period with the initial immunization in complete Freund's adjuvant and all subsequent immunizations in incomplete Freund's adjuvant. As shown in FIG. 10B, antiserum from one of three rabbits reacted with RAW 264 and J774 cells when FACS studies were performed (FACScan®, Becton Dickinson, Lincoln Park, N.J.). Similar staining was noted when an $F(ab')_2$ fragment of purified IgG prepared as described by Andrew and Titus (Current Protocols in Immunology, eds. New York: John Wiley & Sons, pp.2.8.5, 1991) was used in place of whole serum. By contrast, LR9 cells failed to stain with the anti-murine CD14 antibody. Similarly, $F(ab')_2$ IgG fragments prepared from non-immune rabbit IgG failed to stain any of the cell lines (not shown).

An additional experiment to evaluate the ability of the anti-murine CD14 IgG antibody to recognize native murine CD14 was performed by using as a source of native murine CD14 a cell-free supernatant from RAW or J774 cells ($5 \times 10^6$ cells/ml) treated with 1 U/ml phosphatidylinositol-specific phospholipase C (PI-PLC, Sigma) for 1 hour at 37° C. Cell-free supernatants were also prepared from LR9 or murine fibroblast L929 cells treated with PI-PLC. Equal amounts of protein from these supernatants were subjected to SDS-PAGE and then transferred to nitrocellulose. Immunoblotting was performed using either rabbit anti-murine CD14 IgG obtained as described above or nonimmune IgG and followed by the addition of peroxidase-conjugated goat anti-rabbit IgG. As shown in FIG. 10A, PI-PLC treatment resulted in the release of immunoreactive protein from RAW and J774 cells while a comparable fraction from LR9 and L929 cells failed to react with the anti-murine CD14. The totality of these data support the contention that the anti-murine CD14 antibody recognizes native murine CD14 and that LR9 cells fail to express CD14. In similar tests murine CD14 could not be detected with any of the commercially available anti-hCD14 monoclonal antibodies MY-4, 6303, and 3C10.

22. Preparation of Anti-human CD14 Antibody

Recombinant human sCD14, prepared as described by Han, et al., supra, was immunopurified from cell culture supernatants using immobilized anti-CD14 mAB 63D3 and was used as an antigen to immunize a goat; purified IgG and $F(ab')_2$ IgG fragments were prepared as described by Andrew and Titus, supra. The specificity of this antibody fraction was determined by Western blotting techniques, ELISA (with sCD14 as the antigen), and FACS using transfected CHO cells expressing recombinant CD14 on their surface (not shown).

23. Measurement of Cell Activation

RAW, J774, GG2EE cells as well as peritoneal elicited macrophages (PEM) from C3H/FeJ mice (an LPS-responsive strain) or C3H/HeJ mice (a strain not responsive to LPS) were distributed in sterile microtiter plates (Costar, Cambridge, Mass.) at the density of $2-3 \times 10^5$ cells/well for RAW and J774 cells or $10^5$ cells/well for PEM cells. After 5 hours of incubation, complete RPMI was removed and cells were washed with serum-free RPMI. Different mixtures of (1) LPS, (2) Gram-positive bacterial cell walls, (3) LAM, (4) murine TNFα, and (5) the purified anti-human CD14 antibody fraction described in Example 22 were diluted in serum-free RPMI containing 0.5 mg/ml human serum albumin and added to the wells in duplicate or triplicate. Experiments were performed in 200 μl volume with 5% fetal bovine serum (Sigma) at final concentration.

In some experiments, supernates were sampled after 4 hours for TNF measurements using the WEHI clone 13 bioassay (Espevik). In other experiments, 10 U/ml murine γ-IFN was added to the mixtures and incubations were carried over 15 hours. Supernates were assayed for nitrite production as described by Ding, et al. (*J. Immunol.*, 141:2407–2412, 1988). The different agonists and antibodies did not affect the viability of the cells, as assessed by the colorimetric MTT assay (not shown) (Mosmann, *J. Immunol. Methods*, 65:55–63, 1983).

As shown in FIG. 11, anti-murine CD14 antibody inhibited LPS- or *B. subtilis* cell wall-dependent nitrite production in J774 cells. The LR9 cells were markedly hyporesponsive to stimulation by either LPS or Gram-positive cell walls. Increasing the concentration of LPS to 3 ng/ml or of Gram-positive cell walls to 1000 ng/ml induced nitrite production in these cells, but under these experimental conditions anti-CD14 failed to reduce the response.

Heparinized whole mouse blood was distributed in a microtiter plate (200 μl/well) and incubated in presence of LPS and polyclonal anti-murine CD14 IgG after 4 hours incubation at 37° C., conditioned plasma were assayed for TNF bioactivity using the method of Espevik and Nissen-Meyer, supra. In experiments with THP-1 cells, cells were washed 2 times with serum-free RPMI containing 0.5 mg/ml human serum albumin, resuspended in serum free media, and distributed at the concentration of 5–7×10⁴ cells/well. Fetal bovine serum (Sigma) was added to obtain a final concentration of 5%. Various concentrations of LPS, cell wall preparations, LAM or soluble peptidoglycan were added to the cells with or without antibodies in duplicate, and incubated at 37° C. for 7 hours. Cell free supernates were then sampled and frozen at −20° C. IL-8 was measured with an ELISA as previously described by Standiford, et al. (*J. Immunol.*, 145:1435–1439, 1990), with results as shown in FIG. 13.

IgM expression by 70Z/3 cells was measured as previously described by Lee, et al., supra. Cells were suspended in complete RPMI and distributed in 48-well plates (Costar) at a concentration of 5×10⁵ cells/well in 0.5 ml volume. Stimulation in 5% fetal bovine serum was accomplished by the addition of various concentrations of LPS, *B. subtilis* cell wall preparation, or mycobacterial LAM. IgM expression was assessed FACS analysis after incubation for 18 hours at 37° C. As shown in FIG. 14, like LPS, cell walls and LAM induced a significant increase in the upregulation of IgM when hCD14 was expressed on the surface of the cells, indicating a definite involvement of CD14 in the response of these different agonists.

24. Biochemical Interactions Between Soluble CD14 and Cell Walls or Lipoarabinomannan $^{35}$S-sCD14 was produced using Chinese hamster ovary cells that were transfected with CD14 cDNA according to the method of Han, et al., supra and then incubated with $^{35}$S-methionine (Dupont NEN, Boston, Mass.). The $^{35}$S-sCD14 was purified from cell culture supernatants using immobilized antiCD14 mAb 63D3. Concentration of $^{35}$S-sCD14 was determined by ELISA as described by Pugin, et al., supra, 1993a and found to be >95% pure by SDS-PAGE. Its specific activity was 150 cpm/ng. Binding of $^{35}$S-sCD14 to cell walls was assessed as follows: 120 μg/ml of cell walls from *S. mitis* (insoluble in aqueous solutions) were suspended in phosphate buffered saline (PBS) at a pH 7.3 supplemented with 2 mg/ml of low endotoxin human serum albumin (HSA) and incubated with 120 ng/ml $^{35}$S-sCD14 for 1 hr at 37° C. Cell walls were then pelleted at 4° C. using high speed centrifugation (13,000 g), resuspended, vortexed, washed three times with ice-cold PBS/HSA, and radioactivity was measured in a scintillation counter.

In further experiments it was shown that the fluorescence intensity of ReS95 containing covalently bound fluorescein (FITCReS95-LPS) prepared according to the method of Skelly, et al., supra. is markedly increased after it binds to sCD14. Such changes in fluorescence permit real-time analysis of LPS binding to LPS-binding proteins including sCD14. Mycobacterial LAM was used in this fluorescence-based assay to test for its ability to interfere with binding of FITC-ReS95-LPS to sCD14. In this experiment, a 50- or 250-fold (weight/weight) excess of LAM over LPS was added to 20 ng/ml FITC-ReS95 LPS, in the presence of 0.1 μg/ml purified rabbit LBP and 10 μg/ml recombinant soluble CD14 (0.25 ml final volume). Fluorescence changes were recorded using an SLM 6000 fluorimeter (SLM, Aminco, Urbana, Ill.) using excitation and emission wavelengths of 490 nm and 520 nm, respectively (results not shown).

The foregoing specification, including the specific embodiments and examples, is intended to be illustrative of the present invention and is not to be taken as limiting. Numerous other variations and modifications can be effected without departing from the true spirit and scope of the invention.

What is claimed is:

1. A method of ameliorating one or more symptoms of Gram positive bacterial or mycobacterial sepsis in a subject comprising administering to the subject a therapeutically effective amount of an antibody, wherein the antibody is produced by ATCC Accession No. HB11364 (28C5) or is an antibody having an antigen binding site of HB11364 (28C5).

2. A method of ameliorating Gram positive bacterial or mycobacterial sepsis in a subject comprising administering to the subject a therapeutically effective amount of an antibody, wherein the antibody is produced by ATCC Accession No. HB44 (63D3) or is an antibody having an antigen binding site of HB44 (63D3).

3. A method of ameliorating one or more symptoms of Gram positive bacterial or mycobacterial sepsis in a subject comprising administering to the subject a therapeutically effective amount of an antibody that inhibits binding of Gram-positive toxigenic cell wall components to CD14, and inhibits secretion of tumor necrosis factor by cells of the monocyte macrophage lineage, wherein the antibody is produced by hybridoma ATCC HB44 or ATCC HB11364 or a host cell containing a polynucleotide encoding a 63D3 or 28C5 antibody or an antibody having an antigen binding site of 63D3 or 28C5, thereby treating the sepsis.

* * * * *

UNITED STATES PATENT AND TRADEMARK OFFICE
CERTIFICATE OF CORRECTION

PATENT NO.    : 6,168,790 B1          Page 1 of 1
DATED         : January 2, 2001
INVENTOR(S)   : Ulevitch et al.

It is certified that error appears in the above-identified patent and that said Letters Patent is hereby corrected as shown below:

Column 1,
After the "PARENT CASE TEXT" section, but prior to the "DESCRIPTION" section, please insert the following:

-- GOVERNMENTAL SUPPORT
This invention was made with government support under Contract No. AI 15136, AI 25563, AI 22003, AI 24775, GM28485, GM 37696 and HL23586 by the National Institutes of Health. The government has certain rights in the invention. --

Signed and Sealed this

Second Day of April, 2002

*Attest:*

JAMES E. ROGAN
*Attesting Officer*       *Director of the United States Patent and Trademark Office*